United States Patent
Kim

(10) Patent No.: US 10,052,499 B2
(45) Date of Patent: Aug. 21, 2018

(54) RADIOPHARMACEUTICAL DISTRIBUTION DEVICE

(71) Applicant: UNITEKO CO., LTD., Gwangju-si, Gyeonggi-do (KR)

(72) Inventor: Geunmo Kim, Yongin-si (KR)

(73) Assignee: UNITEKO CO., LTD., Gwangju-si, Gyeonggi-do (KR)

( * ) Notice: Subject to any disclaimer, the term of this patent is extended or adjusted under 35 U.S.C. 154(b) by 223 days.

(21) Appl. No.: 14/898,627

(22) PCT Filed: Jan. 29, 2015

(86) PCT No.: PCT/KR2015/000940
§ 371 (c)(1),
(2) Date: Dec. 15, 2015

(87) PCT Pub. No.: WO2015/115816
PCT Pub. Date: Aug. 6, 2015

(65) Prior Publication Data
US 2016/0151642 A1      Jun. 2, 2016

(30) Foreign Application Priority Data

Jan. 29, 2014   (KR) ........................ 10-2014-0011499

(51) Int. Cl.
*A61N 5/10*    (2006.01)
*G21F 5/015*   (2006.01)
(Continued)

(52) U.S. Cl.
CPC ............ *A61N 5/1007* (2013.01); *A61J 3/002* (2013.01); *A61M 5/007* (2013.01);
(Continued)

(58) Field of Classification Search
CPC ........... A61M 5/007; A61N 2005/1021; G21F 5/015; G21F 5/018; G21G 1/0005; G21H 5/02
See application file for complete search history.

(56) References Cited

U.S. PATENT DOCUMENTS

2005/0085682 A1   4/2005   Sasaki et al.
2009/0131862 A1*  5/2009   Buck .................. A61M 5/1407
                                                              604/67
(Continued)

FOREIGN PATENT DOCUMENTS

JP       06048319 B2    6/1994
JP     2002306609 A    10/2002
(Continued)

OTHER PUBLICATIONS

International Search Report for PCT/KR2015/000940 dated Apr. 22, 2015.
(Continued)

*Primary Examiner* — Thaddeus Cox
(74) *Attorney, Agent, or Firm* — Hauptman Ham, LLP

(57) ABSTRACT

The present invention relates to a radiopharmaceutical distribution device. Thus, the present invention provides the radiopharmaceutical distribution device comprising: a vial for storing an object selected from radiopharmaceuticals or radioactive isotopes; an object supply unit which checks radioactivity by extracting the object stored inside the vial as much as a set amount so as to temporarily store or discharge the same, and which measures radioactivity of the residual object of the discharged object; a saline solution supply unit which is selectively communicated with the object supply unit so as to discharge a saline solution that is to be mixed with the extracted object; and an injection part for storing the object having a specific radioactivity and discharged from (Continued)

the object supply unit and the saline solution of a set volume discharged from the saline solution supply unit in a mixed state.

11 Claims, 28 Drawing Sheets

(51) Int. Cl.
*A61J 3/00* (2006.01)
*G21F 5/018* (2006.01)
*G21F 5/06* (2006.01)
*A61M 5/14* (2006.01)
*A61M 5/145* (2006.01)
*G21G 1/00* (2006.01)
*A61M 5/00* (2006.01)
*A61M 5/19* (2006.01)

(52) U.S. Cl.
CPC ........ *A61M 5/1407* (2013.01); *A61M 5/1452* (2013.01); *A61M 5/19* (2013.01); *G21F 5/018* (2013.01); *G21F 5/06* (2013.01); *G21G 1/0005* (2013.01); *A61N 2005/1021* (2013.01); *A61N 2005/1074* (2013.01); *A61N 2005/1094* (2013.01)

(56) References Cited

U.S. PATENT DOCUMENTS

2010/0030009 A1      2/2010   Lemer
2010/0030074 A1*     2/2010   Imai ................. A61M 5/31501
                                                            600/432

FOREIGN PATENT DOCUMENTS

JP           05228181 B2     7/2013
KR        1020070114693 A   12/2007

OTHER PUBLICATIONS

European Search Report dated Oct. 28, 2016 corresponding to Europe Application No. 15743141.2.

* cited by examiner

RADIOPHARMACEUTICAL DISTRIBUTION DEVICE

CROSS REFERENCE TO RELATED APPLICATION

This application claims the priority of Korean Patent Application No. 10-2014-0011499 filed on Jan. 29, 2014 in the Korean Patent and Trademark Office. Further, this application is the National Phase application of International Application No. PCT/KR2015/000940 filed on Jan. 19, 2015, which is incorporated herein by reference in its entirety.

TECHNICAL FIELD

The present invention relates to a radiopharmaceutical distribution device and to a radiopharmaceutical distribution device supplying, distributing, and packaging radiopharmaceuticals.

BACKGROUND ART

Generally, radioactive materials such as a radioactive isotope, used in a sample such as blood collected from a human body or directly injected into a human body for a purpose of diagnosis, treatment, or medical research, and a labeled compound thereof are referred to as radiopharmaceuticals.

A theory of medical use of radioactive materials is first introduced by G. Hevesy in 1913. Radiopharmaceuticals have two characteristics as a medicine and a radioactive material. Of those, as the medicine, firstly, the radiopharmaceutical should be a material appropriate for a purpose of inspection or treatment, secondly, should be nontoxic and should not cause any problem in the future, and lastly, should be currently clinically supplied.

As the characteristic of a radioactive material, firstly, the radiopharmaceutical should be easily operated due to a moderate physical half-life and have less problem due to a short effective half-life, secondly, should be excellent in efficiency and shielding of a measure machine due to moderate energy emitted from the radioactive material, thirdly, has high specific radioactivity, and lastly should be easily purchased and economical.

However, since radiopharmaceuticals generally decay differently from a general medicine, there is a time limit from manufacturing to use.

Currently, the radiopharmaceuticals are used in about 80 types of medical diagnoses and researches. About 30 types of radiopharmaceuticals are produced in Korea, and the radiopharmaceuticals are classified into treatment, diagnosis, inside body use, and outside body use according to a purpose of use.

A diagnostic drug for inside body use is used for a morphological diagnosis or measurement of a function of a specific organ and an internal organ by radioactive diagnostic medicine injected into an inside of human body using a characteristic as a chaser of radioactive isotope and for measurement of an amount of specific material in a human body, such as blood, or a flow expansion time, and is used for an eating rate, a dissipation rate, a metabolic rate and the like in each organ.

Since a diagnostic drug for outer body use is used to perform quantitative inspection of extremely few physiological active substances existing in blood or urine, a carrier thereof, or an injected medicine, there is no need to consider radioactivity exposure to a patient. Also, since the amount of used radioactive isotope is extremely few, the diagnostic drug for outer body use is conveniently handled. The measuring method includes a competitive reaction, a competitive protein binding assay (CPBA), a radioimmunoassay (RIA), a radioreceptor assay (RRA) and the like, and the diagnostic drug for outer body use is provided as a radiopharmaceutical kit.

In the object such as the radioactive isotope or radiopharmaceuticals, the amount of radioactivity of the object stored in a storage container is first measured whenever necessary, and the amount of the object in which a unit dose of radioactivity is included is calculated, and thus the calculated amount of the object is moved to a medicine bottle or an injector to be used.

The technique of distributing such an object is disclosed in Korean Patent No. 10-0740215 in detail.

However, a conventional apparatus or method of distributing an object has problems of an inconvenience in that an amount of radioactivity included in the object should be measured, accuracy in distributing a set amount of the object at a set concentration is decreased, and a safety accident in which a user is excessively exposed to the radioactivity frequently occurs.

DISCLOSURE

Technical Problem

The present invention is to solve the problems, and an object of the present invention is to provide a radiopharmaceutical distribution device capable of dispensing radiopharmaceuticals into various containers or automatically supplying, distributing, injecting, and packaging the radiopharmaceuticals.

Technical Solution

It is an aspect of the present invention to provide a radiopharmaceutical distribution device including: a vial storing an object selected from a radiopharmaceutical or a radioactive isotope; an object supply unit checking radioactivity by extracting a set amount of the object stored in the vial, temporarily storing or discharging the object, and measuring radioactivity of the object left after the discharging of the object; a saline solution supply unit selectively in communication with the object supply unit and discharging a saline solution to be mixed with the extracted object; and an injection unit storing the object with specific radioactivity discharged from the object supply unit and the saline solution with a set volume discharged from the saline solution supply unit in a mixed state, The object supply unit may include a measuring unit checking radioactivity by receiving the object received from the vial, an inner mixing container arranged in the measuring unit to temporarily store the supplied object, a first pump suctioning the object from the inner mixing container and discharging the object, and a first control unit controlling a movement route of the object discharged or introduced through the first pump.

The saline solution supply unit may include a storage container storing the saline solution, a second pump suctioning the saline solution from the storage container and discharging the saline solution, and a second control unit controlling a movement route of the saline solution discharged through the second pump.

The first control unit may include a first path connecting the vial with the inner mixing container, a second path having one end connected with the first path between the vial and the inner mixing container and the other end on which the injection unit is arranged, and a first valve arranged at a portion at which the first path and the second path are connected to set an opening and closing direction of the first path and the second path.

The second control unit may include a third path having one end connected to the first path between the vial and the first valve, and a second valve arranged at a portion at which the first path and the third path are connected to set an opening and closing direction of the first path and the third path.

The first control unit may include a first outer mixing container provided to be in communication with the first path between the first valve and the first pump and flexibly increasing its volume so that the saline solution or the object supplied from the first pump is temporarily stored when the first valve is closed in every direction.

The radiopharmaceutical distribution device may further include an expansion preventing unit arranged at an outside of the first outer mixing container and preventing a volume of the first outer mixing container from being flexibly increased when the first valve is opened in one direction.

The first control unit may include a third valve arranged between the vial and the second valve to set an opening and closing direction of the first path, and a second outer mixing container provided to be in communication with the first path between the second valve and the third valve and flexibly increasing its volume so that the saline solution or the object supplied from the first pump is temporarily stored when the third valve is closed.

The radiopharmaceutical distribution device may further include a fourth valve provided on the second path; a fifth valve provided on the third path; and a fourth path having one end connected with the fourth valve and the other end connected with the fifth valve, and further include a third outer mixing container provided to be in communication with the second path between the first valve and the fourth valve and flexibly increasing its volume so that the mixed solution or the object supplied from the first pump is temporarily stored when the fourth valve is closed in every direction.

The radiopharmaceutical distribution device may further include a fourth valve provided on the second path, a fifth valve provided on the third path, and a fourth path having one end connected with the fourth valve and the other end connected with the fifth valve, and further include a sixth valve arranged on the second path and provided to be adjacent to the fourth valve between the first valve and the fourth valve, a fifth path having one end coupled to the sixth valve, and a fourth outer mixing container coupled to be in communication with the other end of the fifth path and flexibly increasing its volume so that the saline solution or the object supplied from the first pump is temporarily stored when the sixth valve is opened so that the second path and the fifth path are in communication with each other.

The radiopharmaceutical distribution device may further include a sixth path having one end connected to the fourth outer mixing container and the other end connected to the inner mixing container, wherein the object or the saline solution may be controlled to be circulated from the inner mixing container to the inner mixing container again through the first valve, the sixth valve, and the sixth path by suction force of the first pump.

The radiopharmaceutical distribution device may further include a fourth valve provided on the second path, a fifth valve provided on the third path, a fourth path having one end connected with the fourth valve and the other end connected with the fifth valve, and further include a sixth valve arranged on the second path and provided to be adjacent to the fourth valve between the fourth valve and the injection unit, a fifth path having one end connected to the sixth valve, and a fifth outer mixing container coupled to be in communication with the other end of the fifth path and flexibly increasing its volume so that the saline solution or the object supplied from the first pump is temporarily stored when the sixth valve opens the second path and the fifth path.

The vial may include a first shield preventing the radioactivity from being exposed to the outside by covering the outside to be attached or detached.

The object supply unit may include a second shield interposed between the inner mixing container and the measuring unit to prevent the radioactivity from being measured from the outside of the inner mixing container.

The inner mixing container may be made of an elastic material to allow a volume of the object or the saline solution to be flexibly increased when the object or the saline solution is temporarily stored.

The injection unit may include an injector storing the object or a mixed solution of the object and the saline solution and a cover member coupled to be attached to or detached from the injector and covering an outside of the injector to shield radioactivity emitted from the object stored in the injector.

The injector may include a main body including an inlet, provided on one end thereof to store the object or the mixed solution in the main body, and made of a transparent or translucent material, a push rod partially or entirely inserted into the main body and pressurizing the mixed solution or the object stored in the main body to be discharged to the outside through the inlet by reciprocating, a first support member coupled to the other end of the main body and protruding to be fixed to an inside of the cover member, a second support member coupled at one end of the push rod to be opposite to the first support member and protruding to be fixed to the inside of the cover member, and a cap selectively coupled to the inlet and preventing the saline solution or the object stored in the main body from being leaked to the outside.

The cover member may include a first shield member provided to cover one side of the injector and having an exposure hole so that the other end of the main body or a part of the cap is exposed to the outside, and a second shield member slidably coupled on the first shield member and provided to selectively cover the other side of the injector.

The radiopharmaceutical distribution device may further include a capturing unit arranged to be adjacent to the other end of the main body and confirming a state in which the object or the saline solution is supplied to the injector.

The capturing unit may include a lens member capturing an image of the saline solution or the object injected into the other end of the main body, a plurality of mirror members provided so that the lens member can capture an indirectly reflected phase, and a sensor member detecting that the saline solution or the object injected into the other end of the main body approaches a set range by reading the image captured through the lens member.

Advantageous Effects

The radiopharmaceutical distribution device according to the present invention can be safely used by fundamentally blocking a situation in which radioactivity is directly exposed to a user, can control the concentration and amount of an object, most of all, when the object is distributed, can easily control the amount of the object to a required amount even if the same amount of radioactivity is provided, and can quickly distribute the object by not measuring the amount of radioactivity of the object every time.

MODES OF THE INVENTION

Hereafter, exemplary embodiments according to the present invention will be described in detail with reference to the accompanying drawings. Prior to this, terms and words used in this specification and claims should not be interpreted as limited to commonly used meanings or meanings in dictionaries and should be interpreted with meanings and concepts which are consistent with the technological scope of the invention based on the principle that the inventors have appropriately defined the concepts of terms in order to describe the invention in the best way.

Figure 1:
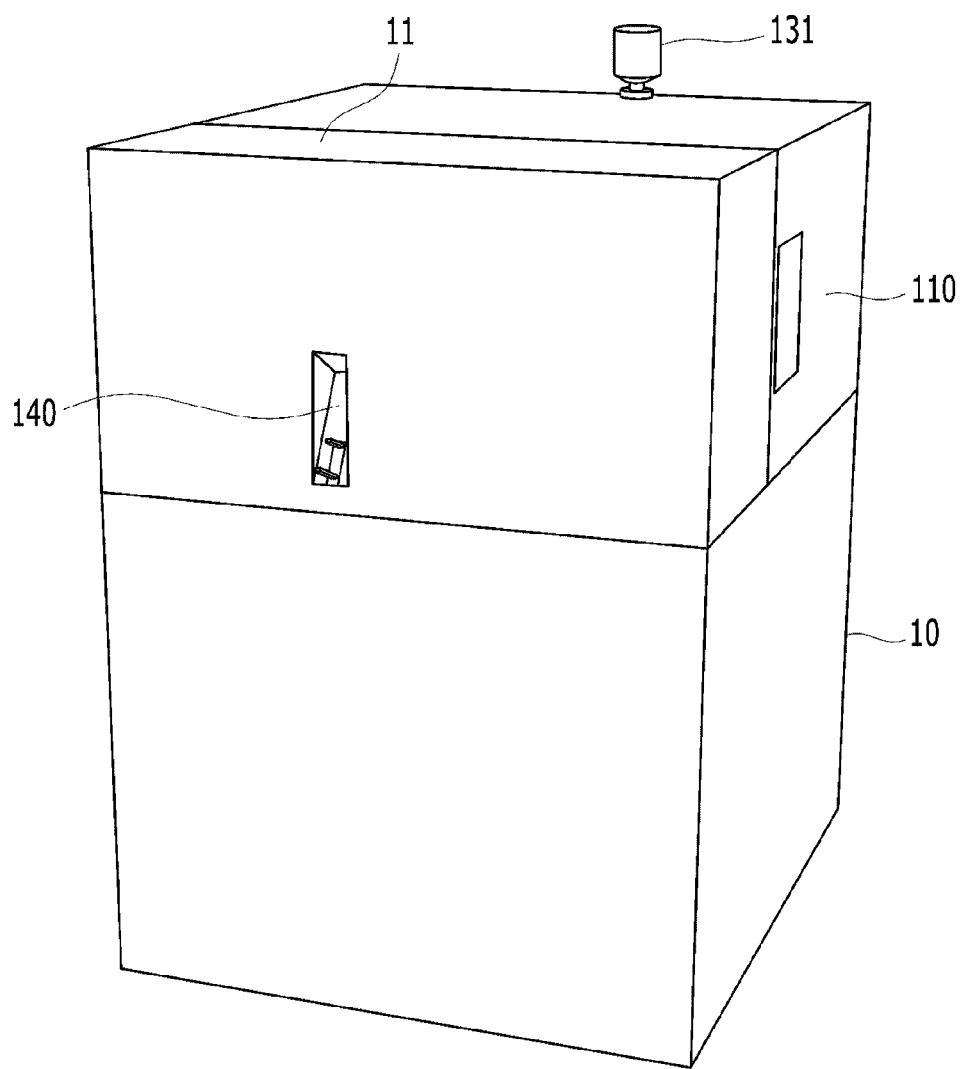
FIG. 1 is a perspective view of a radiopharmaceutical distribution device according to a first embodiment of the present invention.
Figure 2:
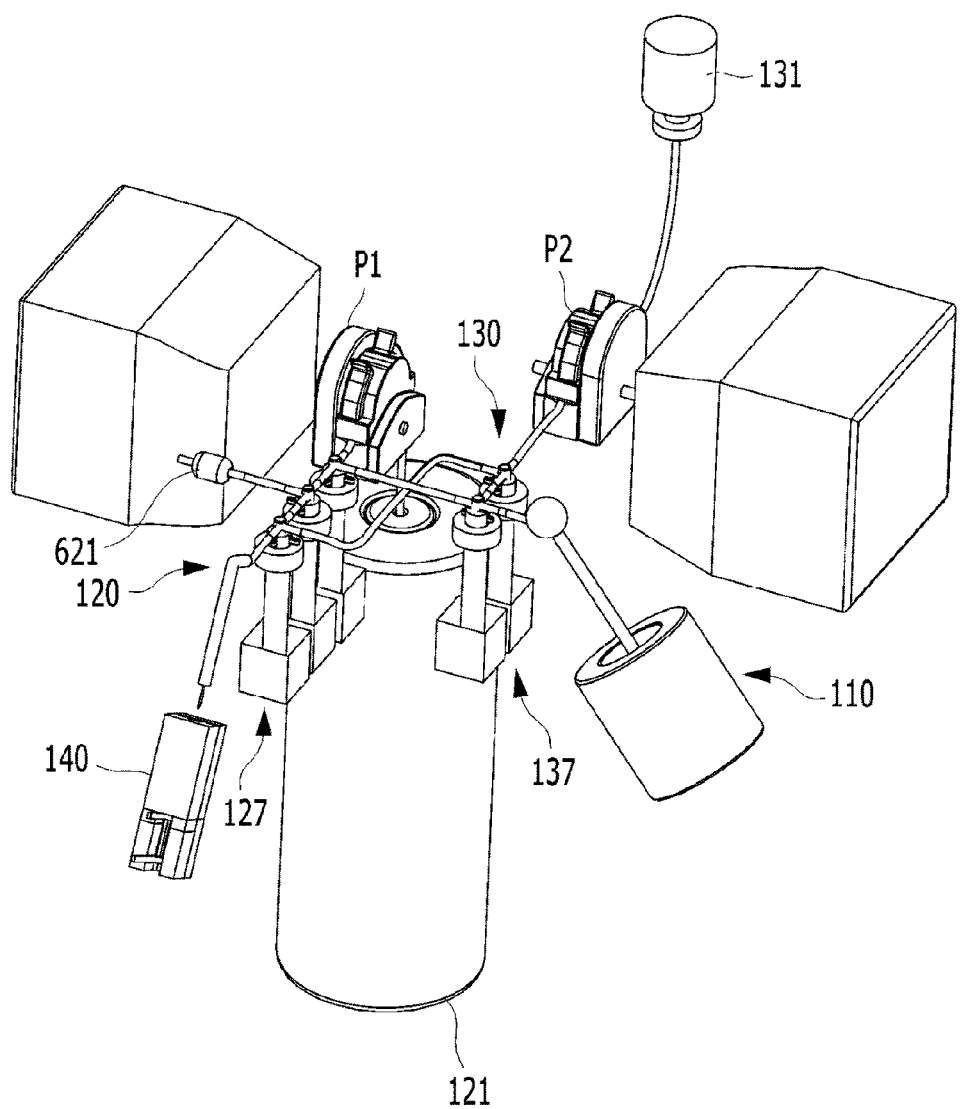
FIG. 2 is a perspective view illustrating an inside of the radiopharmaceutical distribution device shown in FIG. 1.

FIG. 1 is a perspective view of a radiopharmaceutical distribution device 100 according to a first embodiment of the present invention, and FIG. 2 is a perspective view illustrating an inside of the radiopharmaceutical distribution device 100 shown in FIG. 1.

Referring to FIGS. 1 and 2, the radiopharmaceutical distribution device 100 according to the present invention includes: a vial 110 storing an object selected from a radiopharmaceutical or a radioactive isotope, an object supply unit 120 checking radioactivity by extracting a set amount of the object stored in the vial 110, temporarily storing or discharging the object, and measuring radioactivity of the object left after discharging the object; a saline solution supply unit 130 selectively communicating with the object supply unit 120 and discharging a saline solution that is mixed with the extracted object; and an injection unit 140 storing the object with a specific radioactivity discharged from the object supply unit 120 and the saline solution with a set volume discharged from the saline solution supply unit 130 in a mixed state.

In the radiopharmaceutical distribution device 100, as shown in FIG. 1, an outer box 10 forming an appearance includes each component arranged therein, and the vial 110, a storage container 131 storing the saline solution, and the injection unit 140 are arranged to be selectively exposed to the outside. At this time, the vial 110, the storage container 131, the injection unit 140, and the like are configured to be attached or detached, and may be configured to selectively close the vial 110, the storage container 131, and the injection unit 140 by providing a separate door or cover around them.

The outer box 10 is safely shielded from radiopharmaceuticals moving therein along with a door 11 provided at one side of the outer box 10, thereby preventing a user from being exposed to radioactivity as much as possible and also preventing ambient electronic devices from malfunctioning due to exposure of radioactivity, and thus the radiopharmaceuticals may be safely and accurately distributed.

The object supply unit 120 includes a measuring unit 121 checking radioactivity by receiving the object received from the vial 110; an inner mixing container 122 arranged in the measuring unit 121 and temporarily storing the supplied object; a first pump P1 suctioning the object from the inner mixing container 122 and discharging the object; and a first control unit 127 controlling a movement route of the object discharged through the first pump P1.

The saline solution supply unit 130 includes the storage container 131 storing a saline solution; a second pump P2 suctioning the saline solution from the storage container 131 and discharging the saline solution; and a second control unit 137 controlling a movement route of the saline solution discharged through the second pump P2.

The object supply unit 120 and the saline solution supply unit 130 of the radiopharmaceutical distribution device 100 according to the first embodiment of the present invention will be separately described below in detail.

Figure 3:
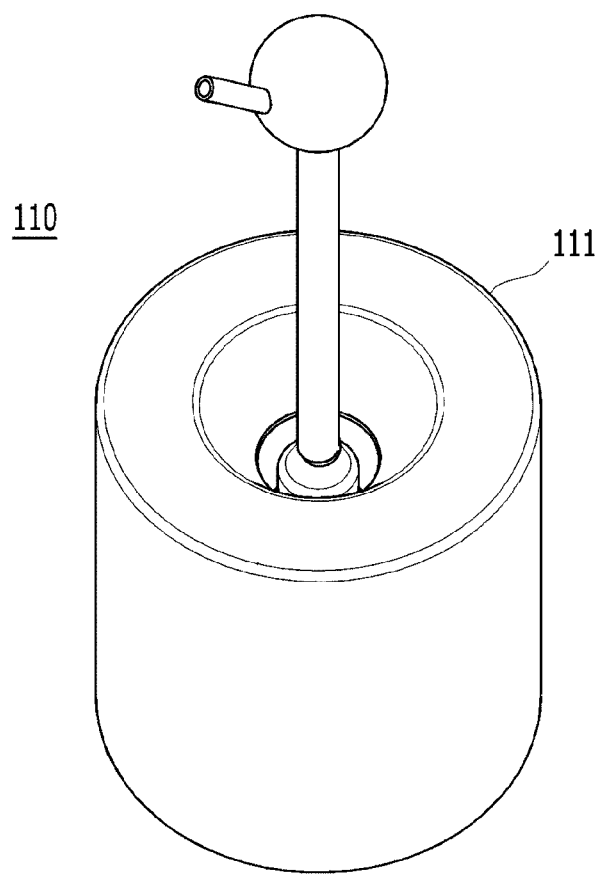
FIG. 3 is a perspective view illustrating a state in which a vial shown in FIG. 2 is inserted into a shield.
Figure 4:
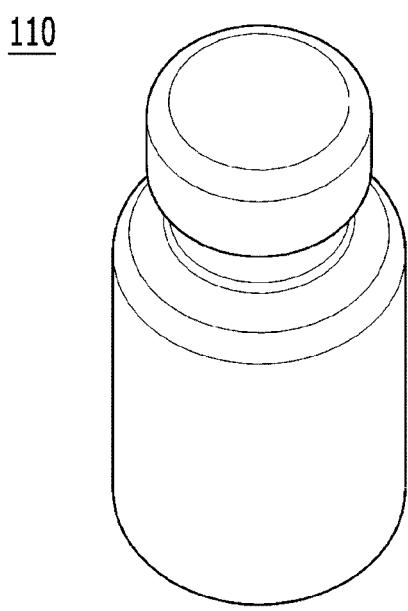
FIG. 4 is a perspective view of the vial of the radiopharmaceutical distribution device of the FIG. 2.

FIGS. 3 and 4 are perspective views illustrating the vial 110 of the radiopharmaceutical distribution device 100 shown in FIG. 2.

Referring to FIGS. 3 and 4, the vial 110 that has a general medicine container shape is formed to store radiopharmaceuticals therein.

As shown in FIG. 3, a first shield 111 is provided at an outer part of the vial 110 to shield radioactivity emitted from the radiopharmaceuticals stored in the vial 110.

The first shield 111 is arranged to firmly surround a remaining part except for a part for extracting radiopharmaceuticals to the outside from the vial 110. The first shield 111 is made of lead (PB), tungsten (W) and the like to prevent penetration of radioactivity.

Figure 5:
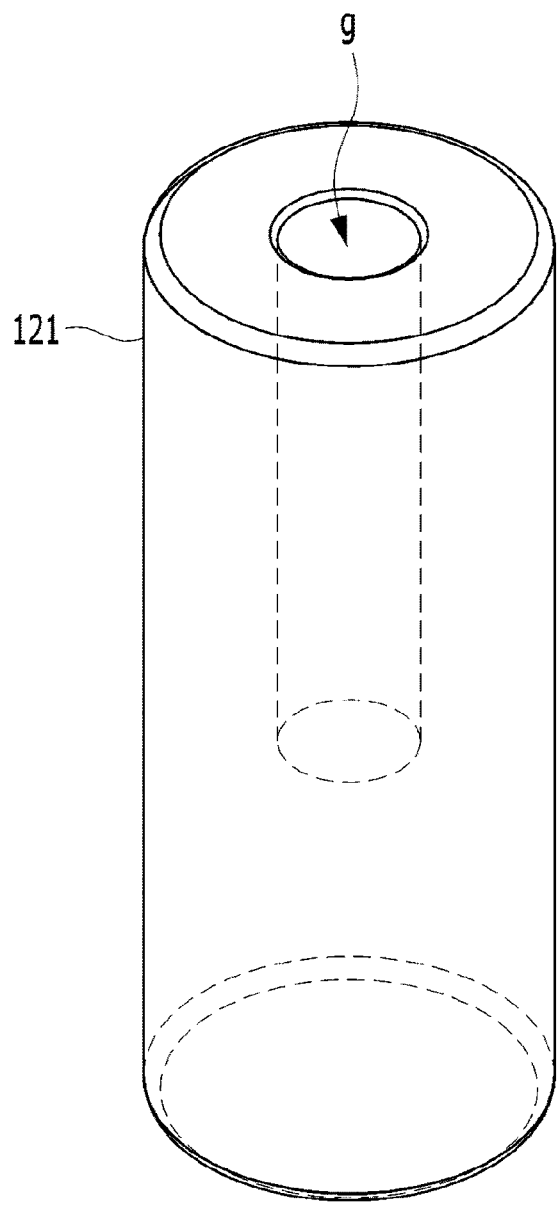
FIG. 5 is a perspective view of a measuring unit of the radiopharmaceutical distribution device shown in FIG. 2.
Figure 6:
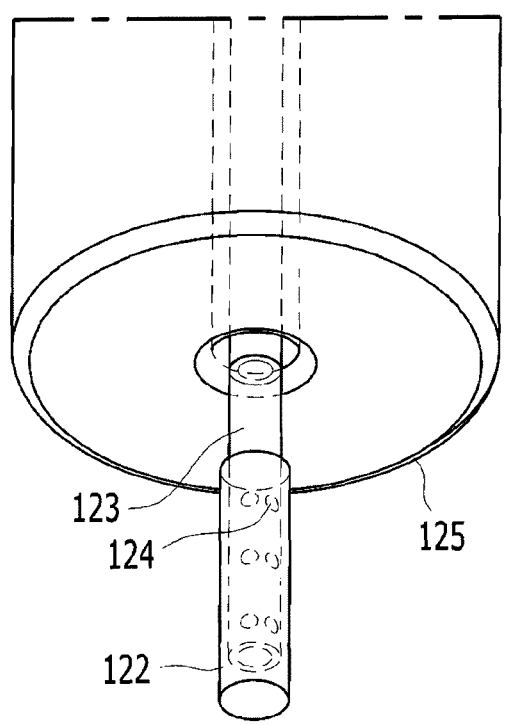
FIGS. 6 and 7 are perspective views illustrating a state in which an inner mixing container arranged in the measuring unit of the radiopharmaceutical distribution device shown in the FIG. 2 is operated.
Figure 7:
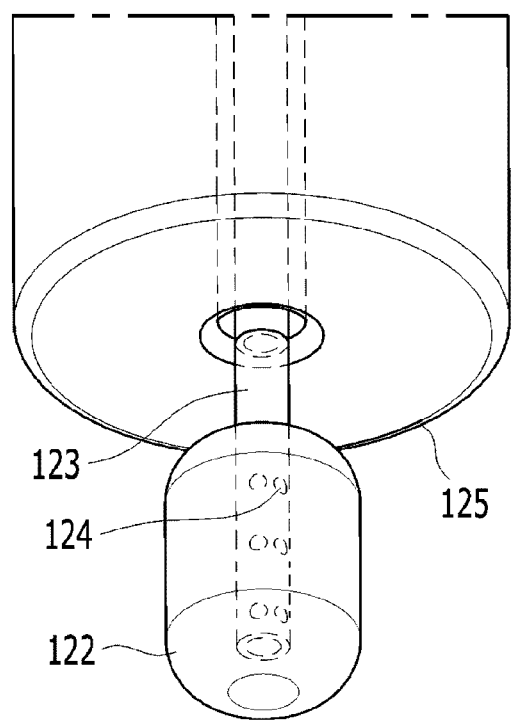
Figure 8:
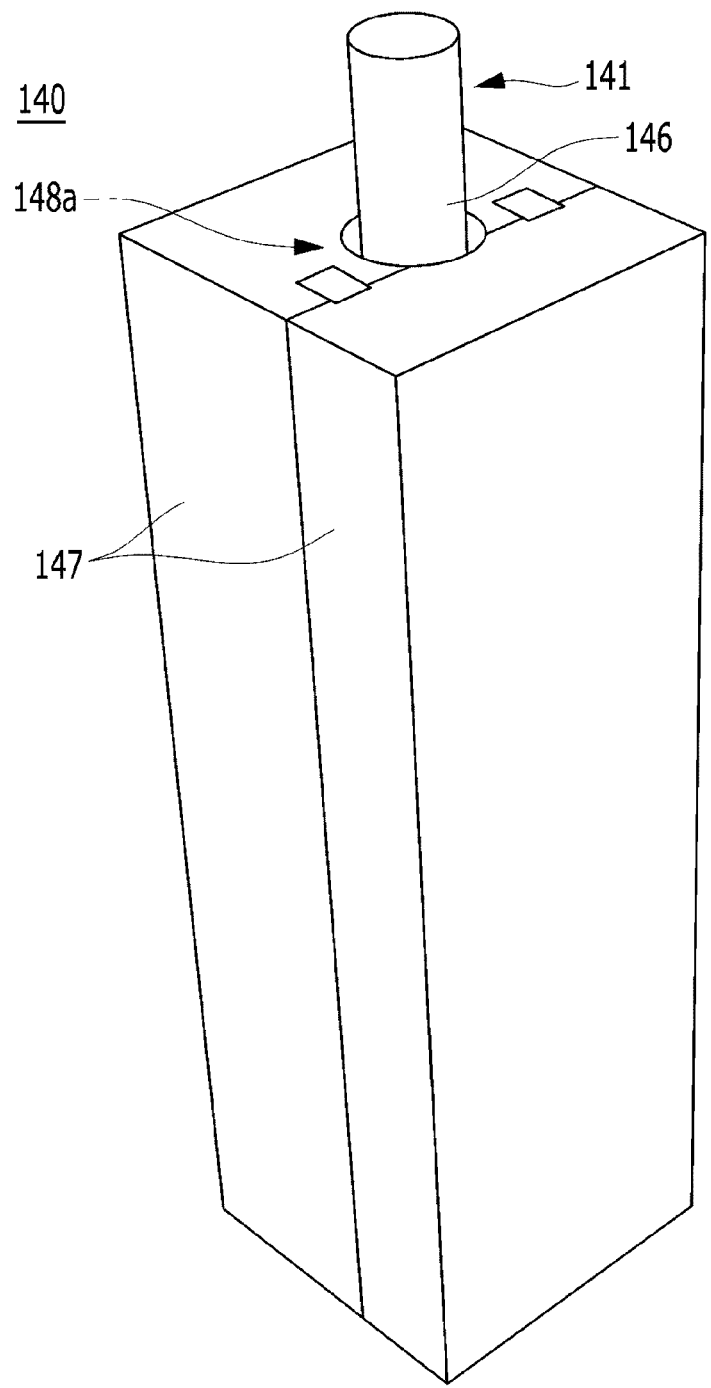
FIGS. 8 to 11 are views of an injection unit of the radiopharmaceutical distribution device.
Figure 9:
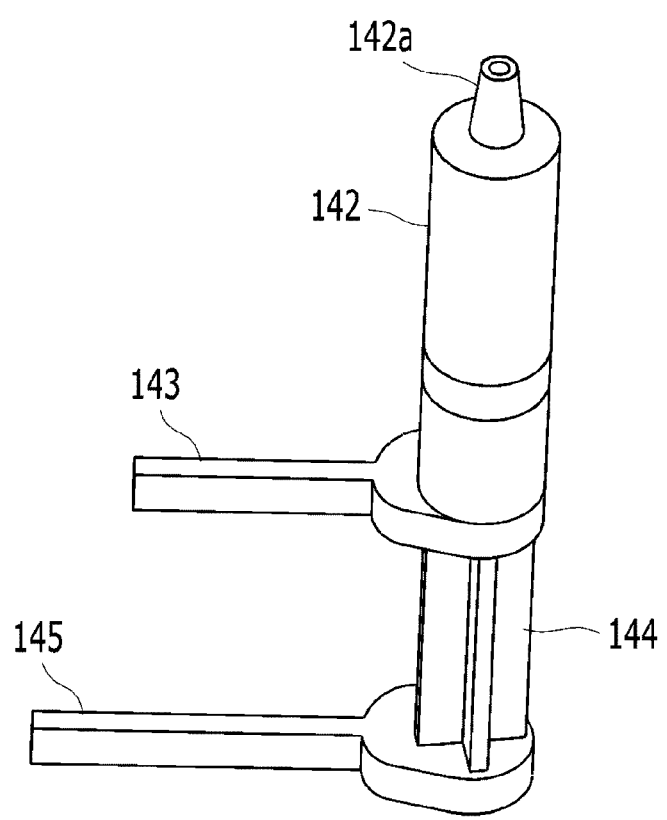
Figure 10:
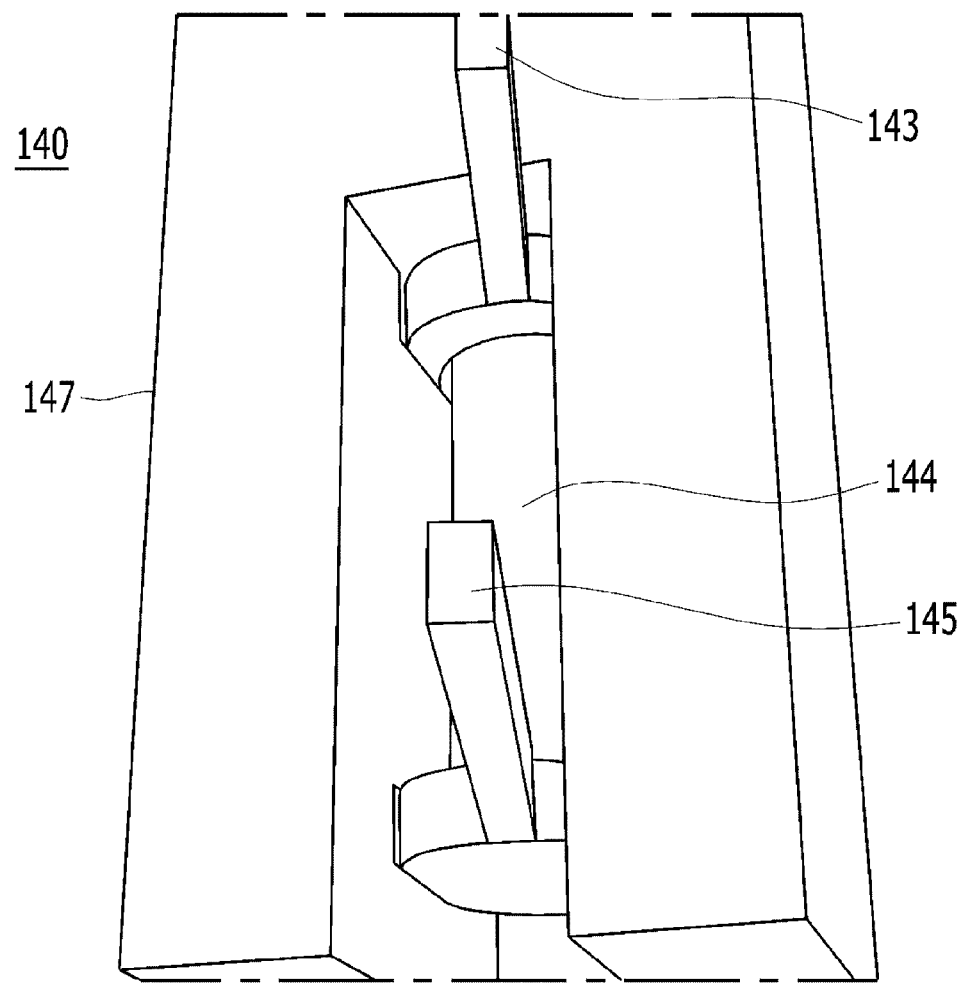

FIG. 5 is a reference view illustrating the measuring unit 121 of the radiopharmaceutical distribution device 100 shown in FIG. 2, and FIGS. 6 and 7 are perspective views illustrating a state in which the inner mixing container 122 arranged in the measuring unit 121 shown in FIG. 5 is operated.

Referring to FIGS. 5 to 7, the measuring unit 121 measures radioactivity in a groove unit g formed therein, and a dose calibrator is used as the measuring unit 121.

The inner mixing container 122 and a connection path 123 connected therewith are inserted into the groove unit g.

A second shield 125 is provided in the groove unit g to shield radioactivity emitted from the connection path 123 connected with the inner mixing container 122.

The inner mixing container 122 is made of an elastic material whose volume is flexibly changed to temporarily store the saline solution or the object supplied through a discharging hole 124 formed at an end of the connection path 123.

That is, the inner mixing container 122 is arranged in the measuring unit 121 to temporarily store the supplied object, and the volume of the saline solution or the stored object may vary.

Of course, the inner mixing container 122 may be made of a non-elastic material (ex. Vinyl pouch) whose volume varies, or a non-elastic material (ex. fixed-shaped container), thereby being replaced with a container with a specific volume.

FIG. 6 shows a state in which the inside of the inner mixing container 122 is empty, FIG. 7 shows a state in which the object or the saline solution introduced in the inner mixing container 122 is expanded. At this time, the discharging holes 124 are formed at an end and an outer circumferential surface of the connection path 123 in a plurality of directions to provide a function in which the object or the saline solution is mixed well in the inner mixing container 122 with each other.

The second shield 125 is simultaneously inserted into the groove unit g along with the inner mixing container 122 to shield radioactivity emitted from the inside of the connection path 123, and thus only radioactivity emitted from the inner mixing container 122 is measured by the measuring unit 121.

In this case, the measuring unit 121 measures the radioactivity as soon as the object or the saline solution is introduced into the inner mixing container 122, measures the discharged amount of radioactivity or the amount of the radioactivity left in the inner mixing container 122 when the object or the saline solution is discharged from the inner mixing container 122 to the outside, and discharges the set amount of the object or saline solution to the outside.

FIGS. 8 to 11 are reference views illustrating the injection unit of the radiopharmaceutical distribution device 100 shown in FIG. 2, and FIGS. 12 to 14 are reference views illustrating a capturing unit 150 capturing an image of the injection unit 140 of the radiopharmaceutical distribution device 100 shown in FIG. 2.

Referring to FIGS. 9 to 14, the object discharged from the inner mixing container 122 or a mixed solution of the object and the saline solution is introduced into the injection unit 140 and then discharged to the outside.

The injection unit 140 includes an injector 141 storing the object and the saline solution in a mixed state, and a cover member 147 coupled so that the injector 141 is attached or detached and covering the outside of the injector 141 to shield radioactivity emitted from the object stored in the injector 141.

The injector 141 includes a main body 142 storing the object or the mixed solution; and a push rod 144 inserted into the main body 142 and provided to reciprocate in a straight direction.

The main body 142 includes an inlet port 142a. At least, the inlet port 142a is made of a transparent or translucent material, or the whole main body 142 may be formed of a transparent or translucent material.

A first support member 143 that fixes the main body 142 to the cover member 147 is provided at the other end of the main body 142. The first support member 143 protrudes from the other end of the main body 142 in a flange shape and extends in one direction to be formed in a pole shape.

The push rod 144 discharges the object or the mixed solution, stored in the main body 142, to the outside through the inlet port 142a by reciprocating while being partially inserted into and discharged from the main body 142.

A second support member 145 is arranged at one end of the push rod 144 to be opposite to the first support member 143 and provided to fix the push rod 144 to an inside of the cover member 147. The second support member 145 is formed in a shape similar to the first support member 143 to provide a function of supporting the injector 141 in the cover member 147.

A cap 146 selectively coupled to the inlet port 142a and preventing the object or the mixed solution, stored in the main body 142, from being discharged to the outside is provided at one end of the main body 142. It is preferable that the cap 146 also be made of a radioactivity-shielding material.

The cover member 147 includes a first shield member 148 covering one side of the injector 141, and a second shield member 149 covering the other side of the injector 141.

The first shield member 148 and the second shield member 149 are slidably coupled to each other, and the injector 141 is positioned in the first shield member 148 and the second shield member 149 to be shielded when the first shield member 148 and the second shield member 149 are completely coupled.

The first shield member 148 includes an exposure hole 148a so that the other end of the main body 142 or a part of the cap 146 is exposed to the outside. The cap 146 is inserted through the exposure hole 148a, or the object or the mixed solution is received from the object supply unit 120 or supplied through the exposure hole 148a.

The second shield member 149 is slidably coupled with the first shield member 148 and is arranged so that one end of the main body 142 or the inlet port 142a is partially opened when the object or the mixed solution is supplied into the main body 142.

Figure 11:
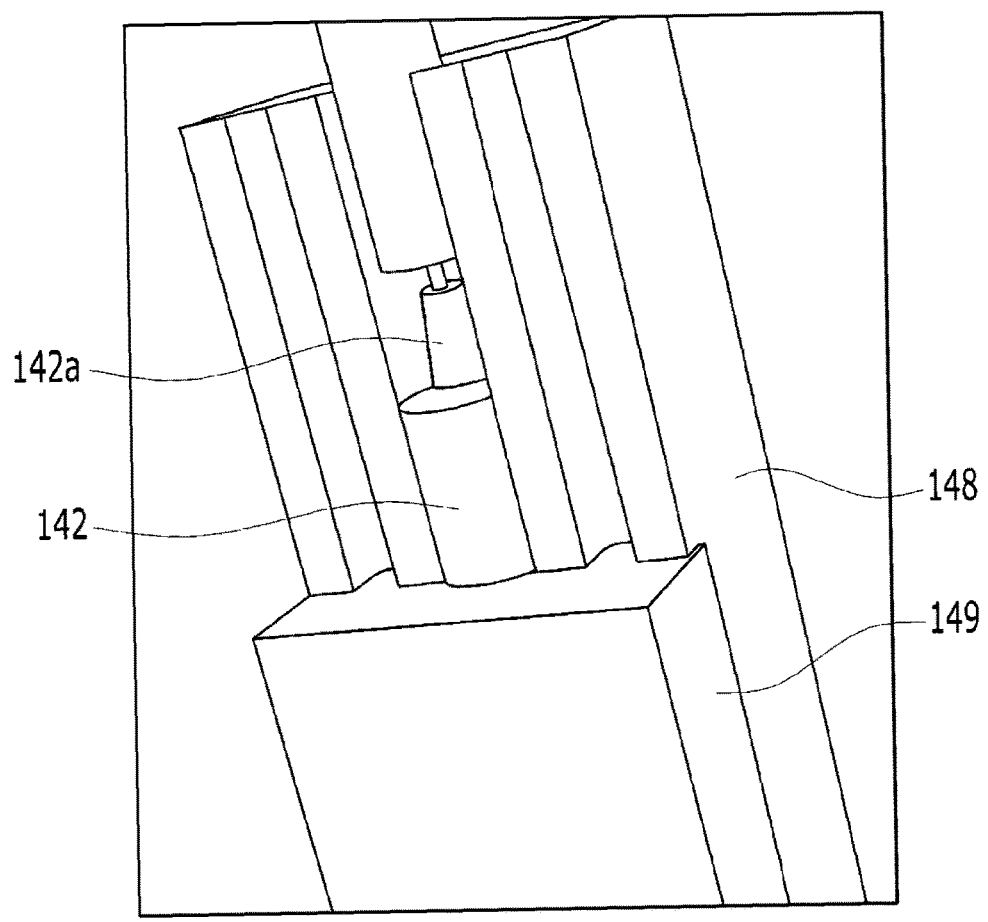
Figure 12:
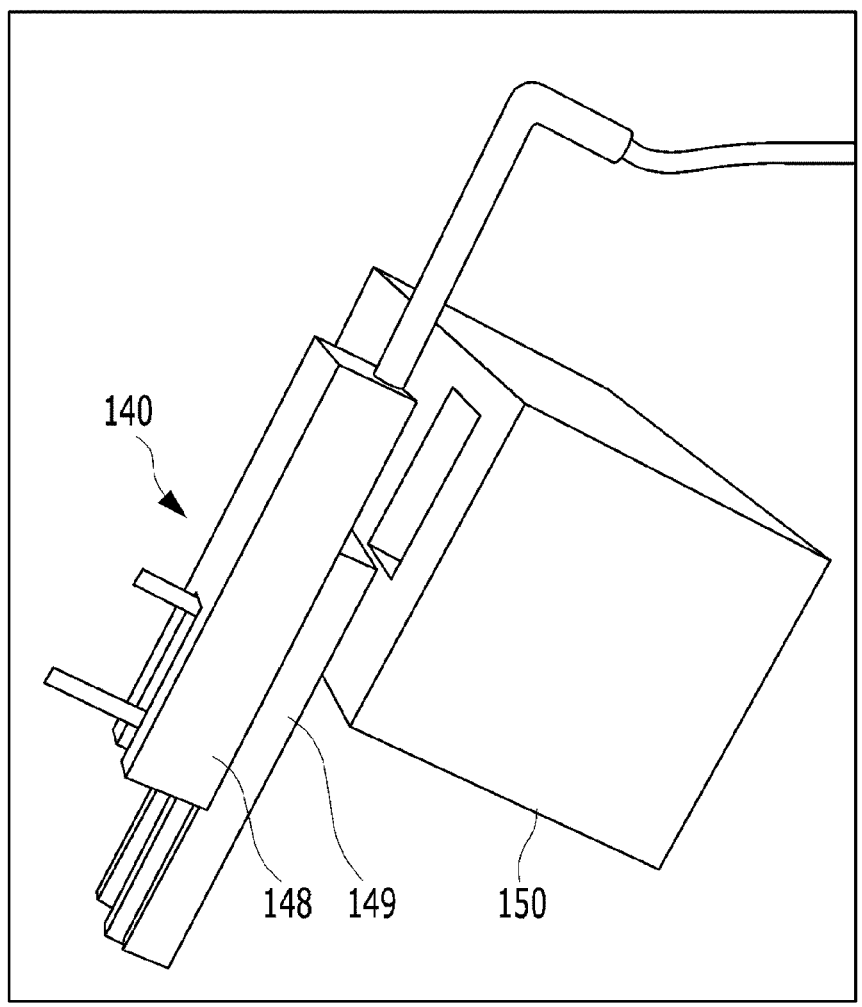
FIGS. 12 to 13 are perspective views illustrating a capturing unit capturing an image of the injection unit of the radiopharmaceutical distribution device.
Figure 13:
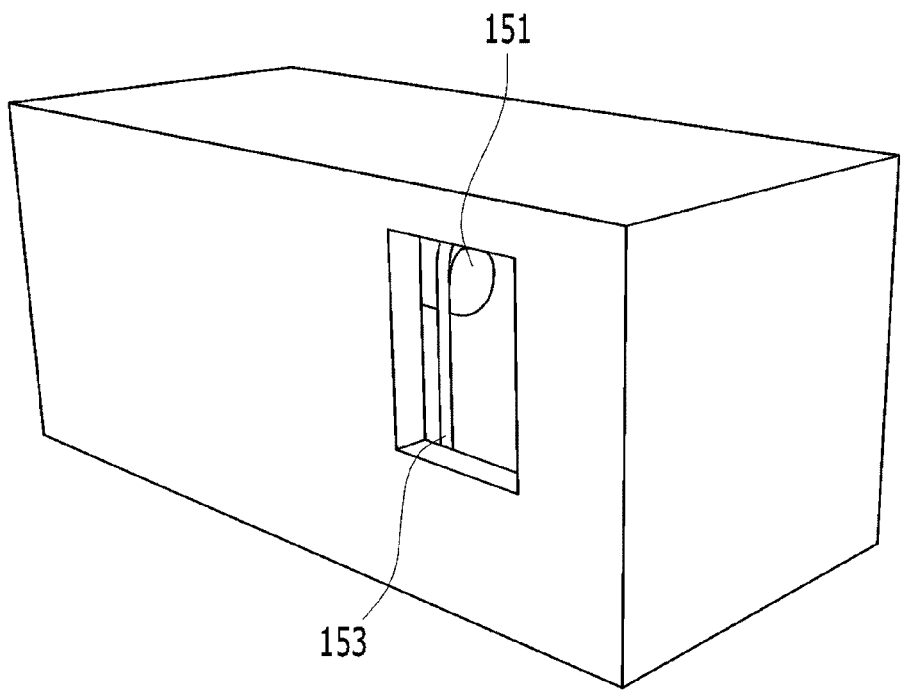
Figure 14:
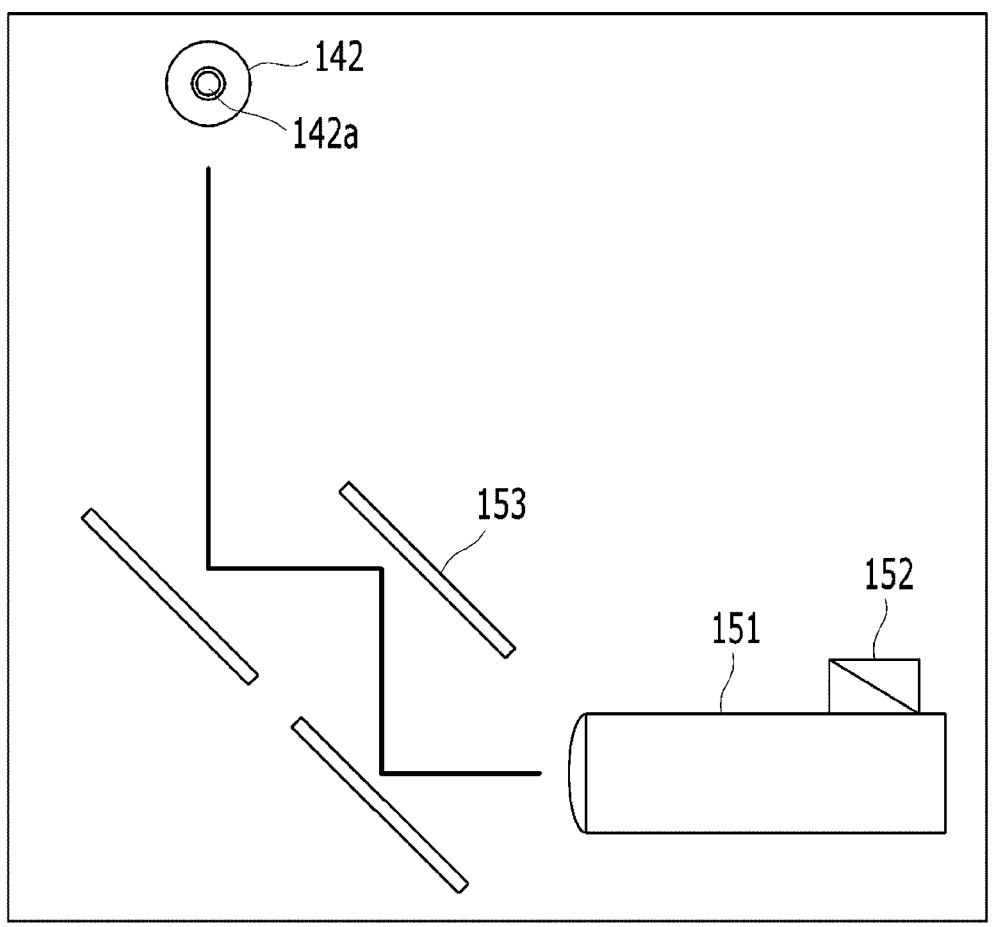
FIG. 14 is a schematic view illustrating a process of capturing an image of the injection unit using the capturing unit.

While the second shield member 149, as shown in FIG. 12, is partially opened on the first shield member 148, as shown in FIG. 11, the inlet port 142a is exposed to the outside and the capturing unit 150 is arranged in a direction of the inlet port 142a.

The capturing unit 150 includes a lens member 151 capturing an image that the mixed solution or the supplied object is introduced to an inside of the injector 141; a plurality of mirror members 152 provided so that the lens member 151 captures an indirectly reflected phase; and a sensor member 153 detecting that the object or the mixed solution injected into the other end of the main body 142 reaches a set range by reading the image captured through the lens member 151.

The mirror member 153 is a means for preventing the lens member 151 from malfunctioning due to radioactivity by securing a distance between the lens member 151 and the inlet port 142a. The mirror member 153 can change an angle and a distance for reflection of the phase according to an installation position of the lens member 15 or a distance between the lens member 151 and the injector 141.

The sensor member 152 measures and controls the amount of the object or mixed solution supplied into the injector by setting a set water level of the object or mixed solution input in advance with a behavior recognition-type program programmed to catch that the mixed solution or the object supplied into the inlet port 142a approaches a set range. Also, the saline solution is supplied into the injector, filled with the set amount of the object or mixed solution, to remove remaining air, and a supplied water level of the saline solution may be also controlled.

Like this, when the capturing unit 150 captures an image of the injector 141, the capturing unit 150 captures an image of the injector 141 using the phase, reflected by the plurality of mirror members 153, rather than directly capturing an image of the injector 141, thereby preventing radioactive contamination of the capturing unit 150.

Figure 15:
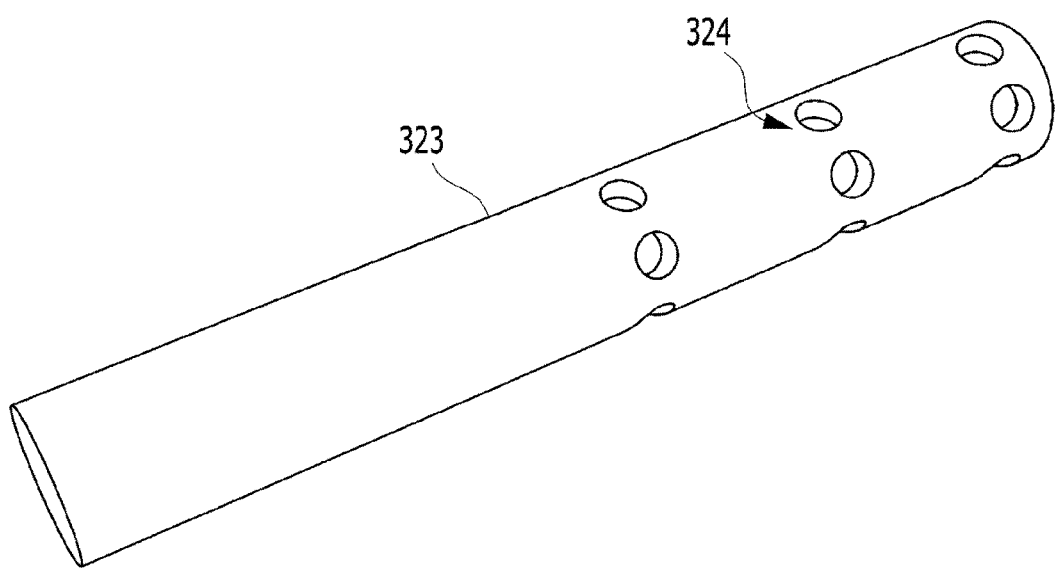
FIGS. 15 to 17 are perspective views illustrating an operation state of an outer mixing container of the radiopharmaceutical distribution device.
Figure 16:
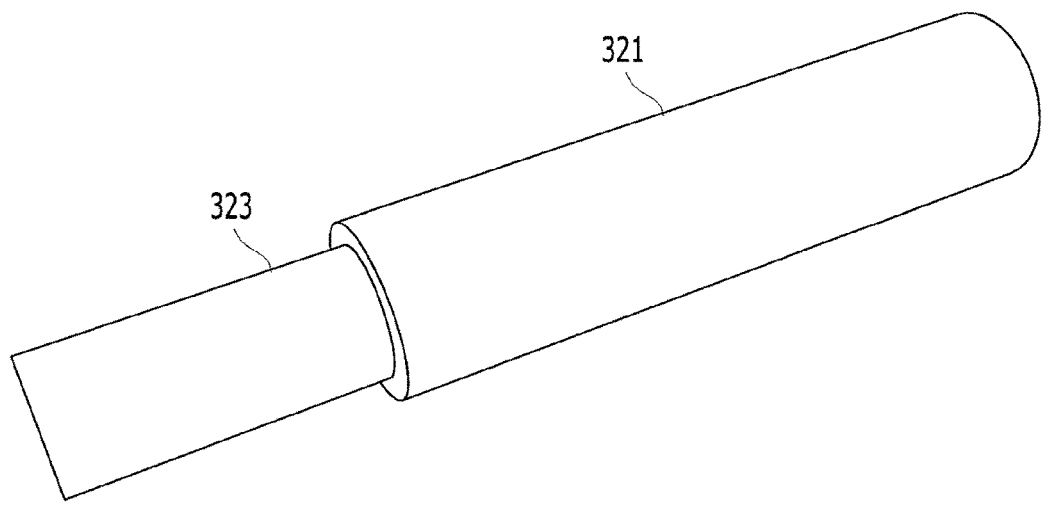
Figure 17:
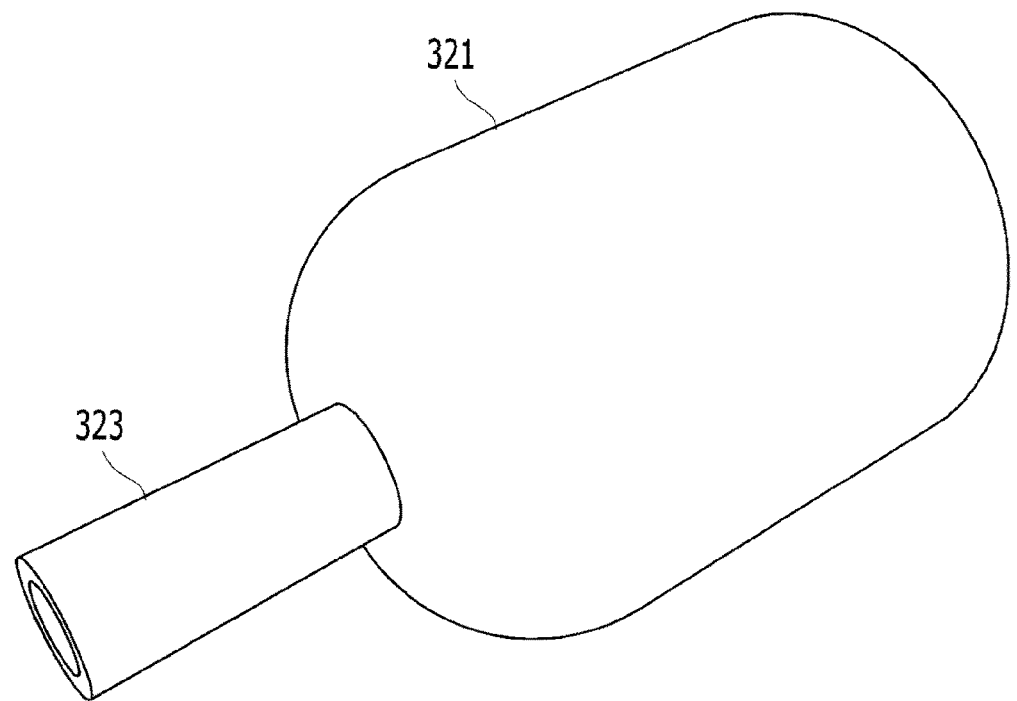

FIGS. 15 to 17 are perspective views illustrating an operation state of an outer mixing container which can be applied to the radiopharmaceutical distribution device 100 shown in FIG. 2.

The outer mixing container is applied with the same components of a first outer mixing container 321 to a sixth outer mixing container 821 shown in FIGS. 20 to 28 used for other embodiments of the present, and the components are installed at different positions. Therefore, the outer mixing containers 321, 421, 521, 621, 621, 721 and 821 illustrated in FIGS. 20 to 28, respectively have different reference numerals, but provide the same function.

Referring to FIGS. 15 to 17, the shape of the outer mixing container is similar to that of the above-described inner mixing container 122. Hereinafter, the first outer mixing container 321 according to the first embodiment of the present invention will be described as an example.

Also, the first outer mixing container 321, like the inner mixing container 122, is made of an elastic material whose volume is flexibly changed to temporarily store the object or the saline solution introduced through discharging holes 324 formed at an end of the path.

The plurality of first outer mixing containers 321 are continuously arranged to temporarily store a large amount of objects or mixed solution.

A detailed function and effect of the first outer mixing container 321 will be described below.

Figure 18:
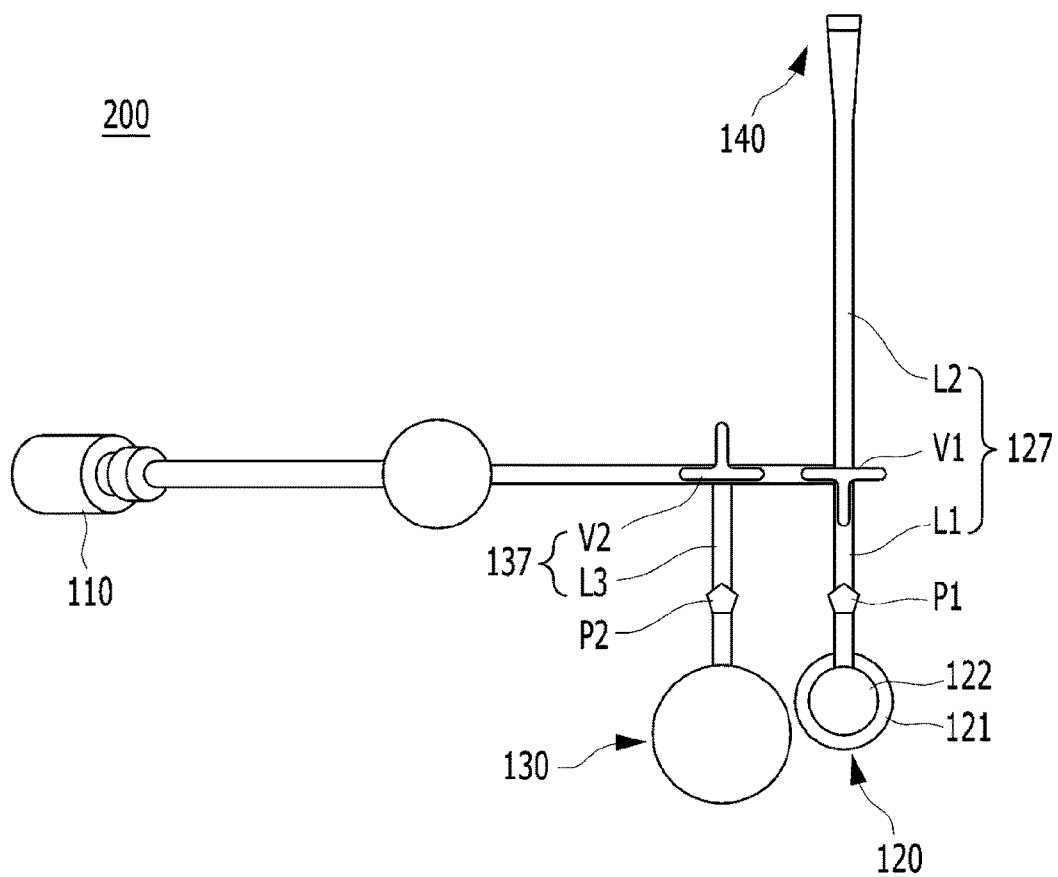
FIGS. 18 and 19 are schematic views illustrating a radiopharmaceutical distribution device according to a second embodiment of the present invention.
Figure 19:
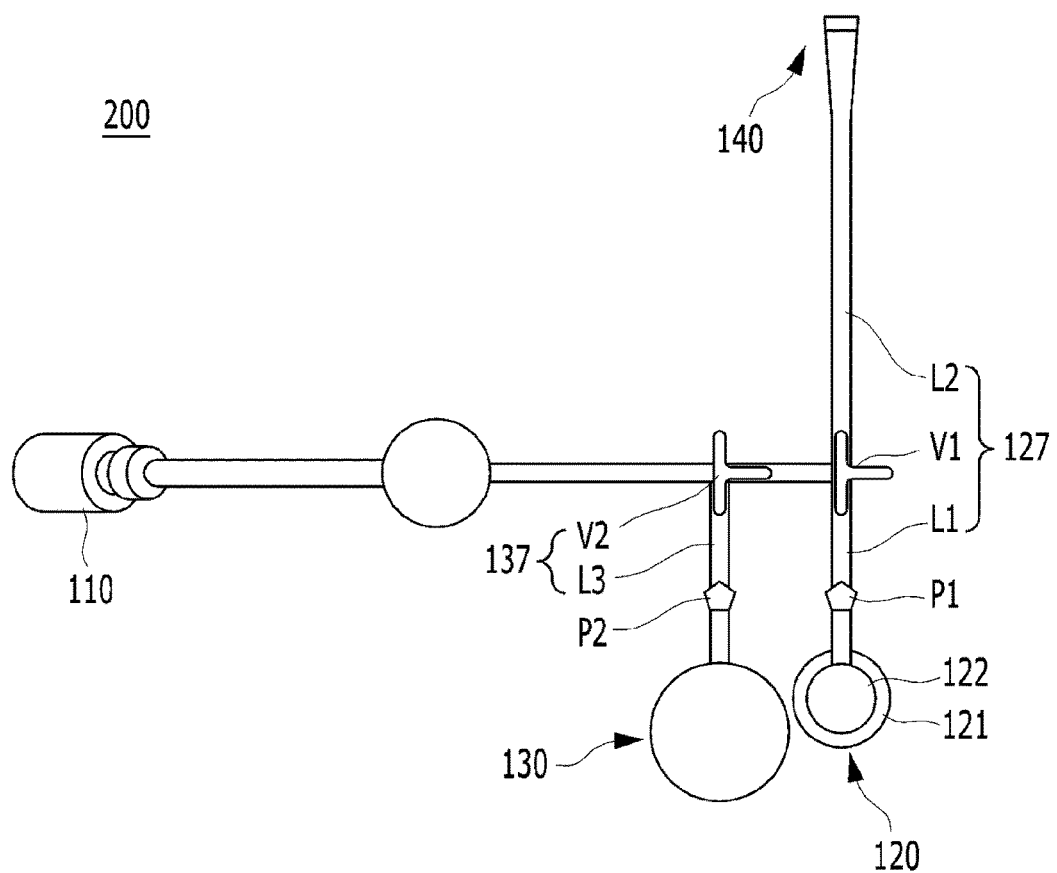

FIGS. 18 and 19 are reference views illustrating a radiopharmaceutical distribution device 200 according to a second embodiment of the present invention. Hereinafter, the same reference numerals as the above-described reference numerals denote the same components.

Referring to FIGS. 18 and 19, the radiopharmaceutical distribution device 200 according to the second embodiment of the present invention includes a vial 110, an object supply unit 120, a saline solution supply unit 130 and an injection unit 140.

The object supply unit 120 includes a measuring unit 121 checking radioactivity by receiving an object received from the vial 110; an inner mixing container 122 arranged in the measuring unit 121 and temporarily storing the supplied object; a first pump P1 suctioning the object from the inner mixing container 122 and discharging the object; and a first control unit 127 controlling a movement route of the object discharged through the first pump P1.

The saline solution supply unit 130 includes a storage container 131 storing a saline solution; a second pump P2 suctioning the saline solution from the storage container 131; and a second control unit 137 controlling a movement route of the saline solution discharged through the second pump P2.

The first control unit 127 includes a first path L1 connecting the vial 110 with the inner mixing container 122, a second path L2 having one end connected with the first path L1 between the vial 110 and the inner mixing container 122 and the other end on which the injection unit 140 is arranged, and a first valve V1 arranged at a portion in which the first path L1 and the second path L2 are connected to set an opening and closing direction of the first path L1 and the second path L2. The second control unit includes a third path L3 having one end connected with the first path L1 between the vial and the first valve V1 and the other end on which the storage container is arranged, and a second valve V2 arranged at a portion in which the first path L1 and the third path L3 are connected to set an opening and closing direction of the first path L1 and the third path L3.

As a moving path of the object is described through such the configuration, as shown in FIG. 18, the first valve V1 is opened to connect the vial 110 with the inner mixing container 122, and the second valve V2 is opened to connect the vial 110 with the first valve V1, and thus the object stored in the vial 110 is suctioned by a suction force of the first pump P1 and is supplied to the inner mixing container 122. In this case, the object or the mixed solution of the object and the saline solution is mixed by repeatedly moving between the vial 110 and the inner mixing container 122 by bidirectional suction force of the first pump P1. Here, although not shown in the figure, a small amount of air introduced into the first path L1 from the vial 110 is blocked or removed through an air detector (not shown) provided between the vial 110 and the second valve V2.

As shown in FIG. 19, the first valve V1 is opened to connect the inner mixing container 122 with the injection unit 140, and thus the mixed solution of the object and the saline solution is supplied to the injection unit 140. In this case, radioactivity of the mixed solution, left in the inner mixing container 122 after the mixed solution is discharged from the inner mixing container 122, is measured, and thus the amount of the discharged mixed solution is calculated.

Lastly, the mixed solution left in the second path L2 is supplied to the injection unit 140 while the second valve V2 is opened to connect the storage container with the injection unit 140.

Accordingly, since it is not necessary to measure radioactivity of the object for every injection like a conventional radiopharmaceutical transferring apparatus, it is expected that a dispensing time can be reduced and a precise amount of radiopharmaceuticals can be dispensed.

Figure 20:
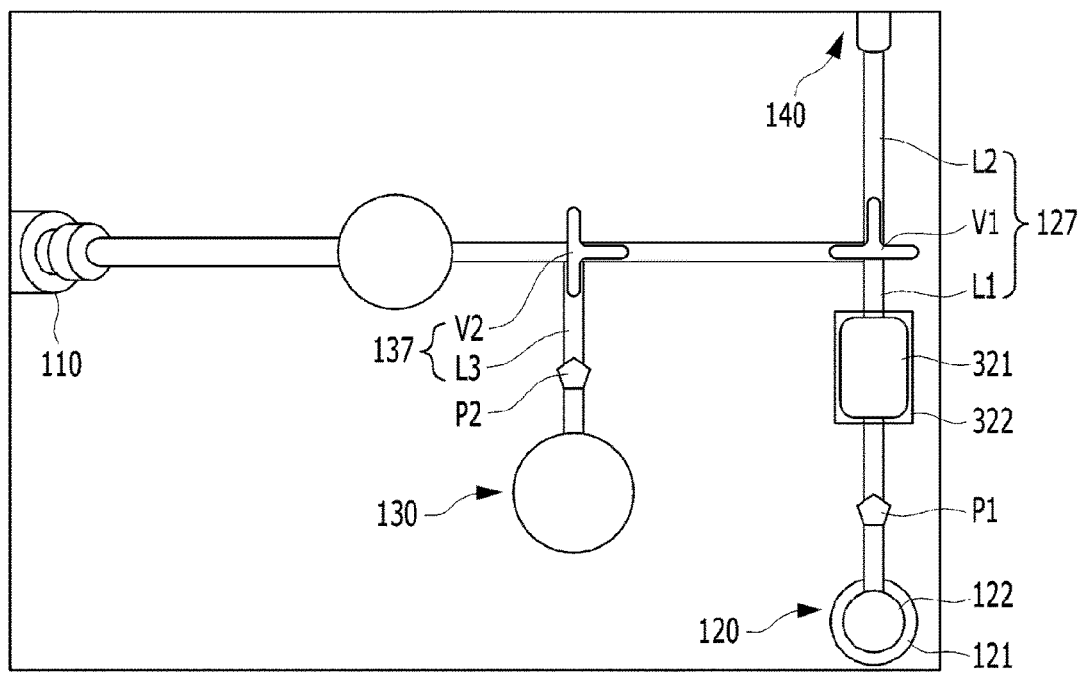
FIG. 20 is a schematic view of a radiopharmaceutical distribution device according to a third embodiment of the present invention.

FIG. 20 is a reference view illustrating a radiopharmaceutical distribution device 300 according to a third embodiment of the present invention. Hereinafter, the same reference numerals as the above-described reference numerals denote the same components.

Referring to FIG. 20, the radiopharmaceutical distribution device 300 according to the third embodiment of the present invention is configured by adding a first outer mixing container 321 to a configuration of the radiopharmaceutical distribution device 200 according to the above-described second embodiment.

In the third embodiment, since a method in which the object is supplied from the vial 110 or the object or the mixed solution is supplied by controlling the second valve V2 is the same as in the second embodiment, redundant description will be omitted.

In the third embodiment, the first control unit 127 is provided to be in communication with the first path L1 between the first valve V1 and the first pump P1, and the first outer mixing container 321 whose volume is flexibly increased is included so that the saline solution or the object supplied from first pump P1 is temporarily stored when the first valve V1 is closed in every direction.

As a moving route of the object is described through the configuration, as shown in FIG. 20, the object supplied from the vial 110 and stored in the inner mixing container 122 is mixed by repeatedly moving the object or the mixed solution of the object and the saline solution between the first outer mixing container 321 and the inner mixing container 122 by bidirectional suction force of the first pump P1 when the first valve V1 is closed in every direction.

The first valve V1 is opened to connect the inner mixing container 122 with the injection unit 140, and thus the mixed solution of the object and the saline solution is supplied to the injection unit 140. In this case, an expansion preventing unit 222 is provided around the first outer mixing container 321 to prevent the first outer mixing container 321 from being expanded when the mixed solution is discharged from the inner mixing container 122. The expansion preventing unit 222 may selectively prevent a volume of the first outer mixing container 321 from being flexibly increased using an air pressure or an oil pressure.

Lastly, the mixed solution left in the second path L2 is supplied to the injection unit 140 along with the supplied saline solution when the second valve V2 is opened to connect the container with the injection unit 140.

Figure 21:
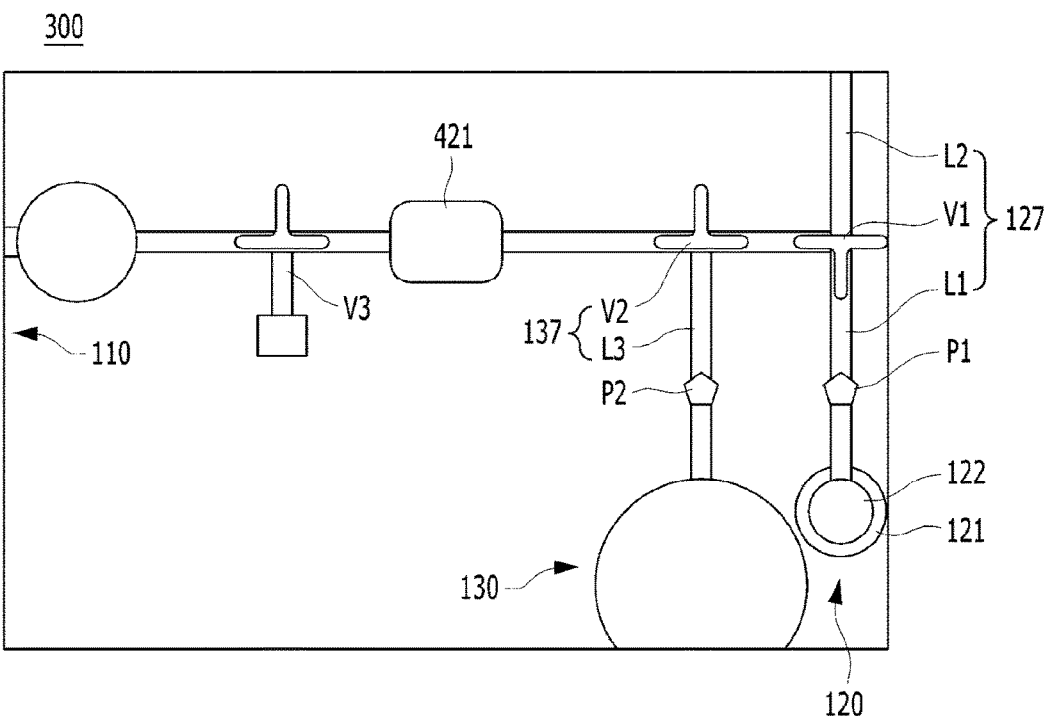
FIG. 21 is a schematic view of a radiopharmaceutical distribution device according to a fourth embodiment of the present invention.

FIG. 21 is a reference view illustrating a radiopharmaceutical distribution device 400 according to a fourth embodiment of the present invention. Hereinafter, the same reference numerals as the above-described reference numerals denote the same components.

Referring to FIG. 21, the radiopharmaceutical distribution device 400 according to the fourth embodiment of the present invention includes a third valve V3 arranged between the vial 110 and the second valve V2 to set an opening and closing direction of the first path L1; and a second outer mixing container 421 provided to be in communication with the first path L1 between the second valve V2 and the third valve V3 and flexibly increasing its volume so that the saline solution or the object supplied from the first pump P1 is temporarily stored when the third valve V3 is closed.

As a movement route of the object is described through the configuration, as shown in FIG. 21, the object passes through the third valve V3 from the vial 110, and is supplied to the inner mixing container 122 through the first valve V1, and the object stored in the inner mixing container 122 is mixed by repeatedly moving the object or the mixed solution of the object and the saline solution between the second outer mixing container 421 and the inner mixing container 122 by bidirectional suction force of the first pump P1 when the third valve V3 is closed in every direction.

The first valve V1 is opened to connect the inner mixing container 122 with the injection unit 140, and thus the mixed solution in which the object and the saline solution are mixed is supplied to the injection unit 140.

Also, when the mixed solution of the object and the saline solution is completely supplied, the second valve V2 is opened to connect the first valve V1 with the storage container, the first valve V1 is opened to connect the second valve V2 with the injection unit 140, and thus the saline solution is supplied and injected along with a part of the objects in the third path L3 and on the first path L1.

Figure 22:
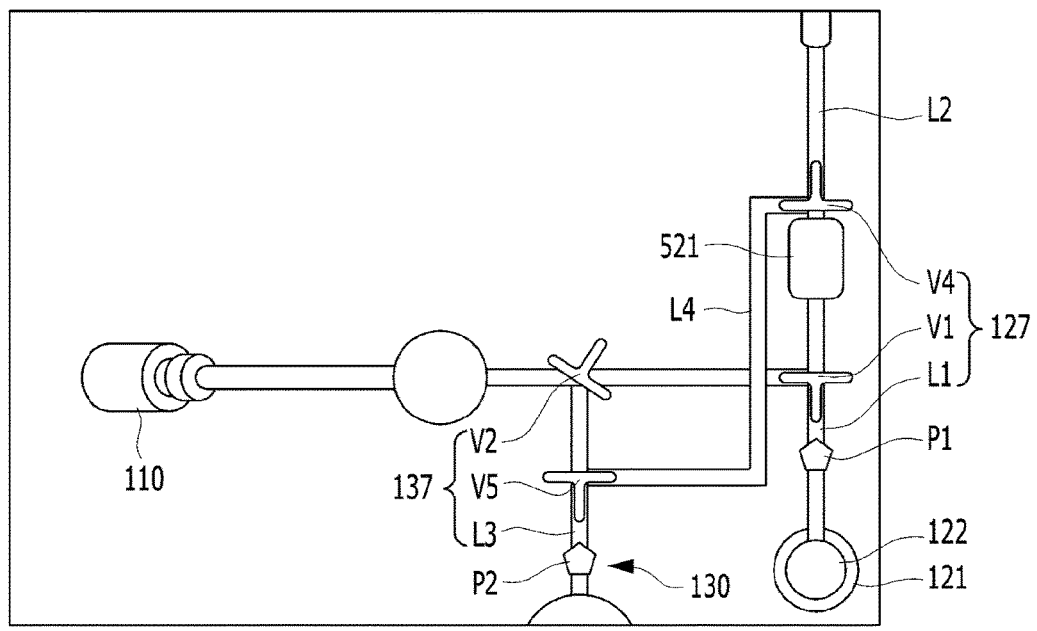
FIG. 22 is a schematic view of a radiopharmaceutical distribution device according to a fifth embodiment of the present invention.
Figure 23:
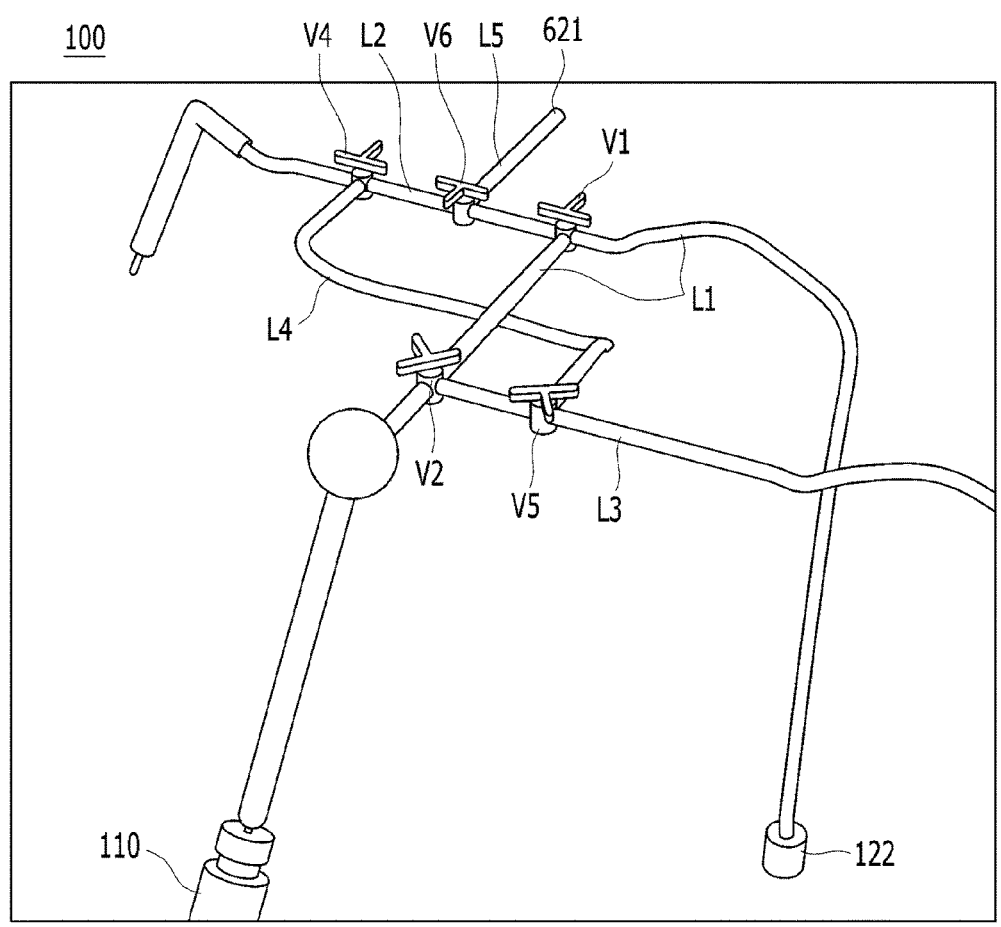
FIGS. 23 to 26 are schematic views illustrating the radiopharmaceutical distribution device according to the first embodiment of the present invention shown in FIG. 2.

FIG. 22 is a reference view illustrating a radiopharmaceutical distribution device 500 according to a fifth embodiment of the present invention. Hereinafter, the same reference numerals as the above-described reference numerals denote the same components.

Referring to FIG. 22, the radiopharmaceutical distribution device 500 according to the fifth embodiment of the present invention includes a fourth valve V4 provided on the second path L2; a fifth valve V5 provided on the third path L3; a fourth path L4 having one end connected with the fourth valve V4 and the other end connected with the fifth valve V5; and a third outer mixing container 521 provided to be in communication with the second path L2 between the first valve V1 and the fourth valve V4 and flexibly increasing its volume so that the mixed solution or the object supplied from first pump P1 is temporarily stored when the fourth valve V4 is closed in every direction.

As a movement route of the object is described through the configuration, as shown in FIG. 22, the object is supplied to the inner mixing container 122 from the vial 110 through the first path L1, the remaining object on the first path L1 is temporarily stored in the inner mixing container 122 while the saline solution is supplied when the second valve V2 is opened to connect the storage container and the first valve V1. While the first valve V1 is opened to connect the inner mixing container 122 and the fourth valve V4, the object or the mixed solution of the object and the saline solution is mixed by repeatedly moving between the third outer mixing container 521 and the inner mixing container 122 by bidirectional suction force of the first pump P1.

Also, when the mixed solution of the object and the saline solution is completely supplied to the injection unit 140, the fourth valve V4 is opened to connect the fifth valve V5 and the storage container, and thus the saline solution is supplied and injected along with a part of the remaining object on the second path L2 through the fourth path L4.

FIGS. 23 to 26 are reference views of the radiopharmaceutical distribution device 100 according to the first embodiment of the present invention shown in FIG. 2. Hereinafter, the same reference numerals as the above-described reference numerals denote the same components.

Referring to FIGS. 23 to 26, the radiopharmaceutical distribution device 100 according to the first embodiment of the present invention includes a fourth valve V4 provided on the second path L2, a fifth valve V5 provided on the third path L3, a fourth path L4 having one end connected with the fourth valve V4 and the other end connected with the fifth valve V5, a sixth valve V6 arranged on the second path L2 and provided to be adjacent to the fourth valve V4 between the first valve V1 and the fourth valve V4, a fifth path L5 having one end coupled to the sixth valve V6, and a fourth outer mixing container 621 coupled to be in communication with the other end of the fifth path L5 and flexibly increasing its volume so that the saline solution or the object supplied from the first pump P1 is temporarily stored when the sixth valve V6 is opened so that the second path L2 and the fifth path L5 are in communication with each other.

Figure 24:
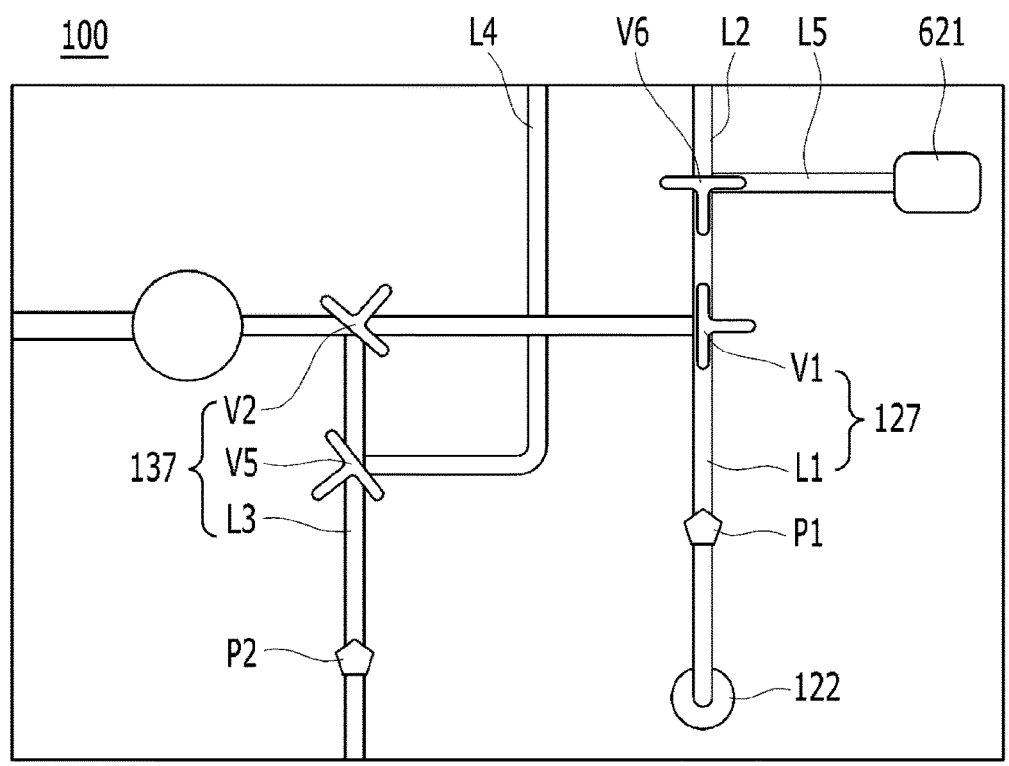

As a movement route of the object is described through the configuration, as shown in FIG. 24, after the object is temporarily stored in the inner mixing container 122, while the first valve V1 is opened to connect the inner mixing container 122 and the sixth valve V6, the object or the mixed solution of the object and the saline solution is mixed by repeatedly moving between the fourth outer mixing container 621 and the inner mixing container 122 by bidirectional suction force of the first pump P1.

Figure 25:
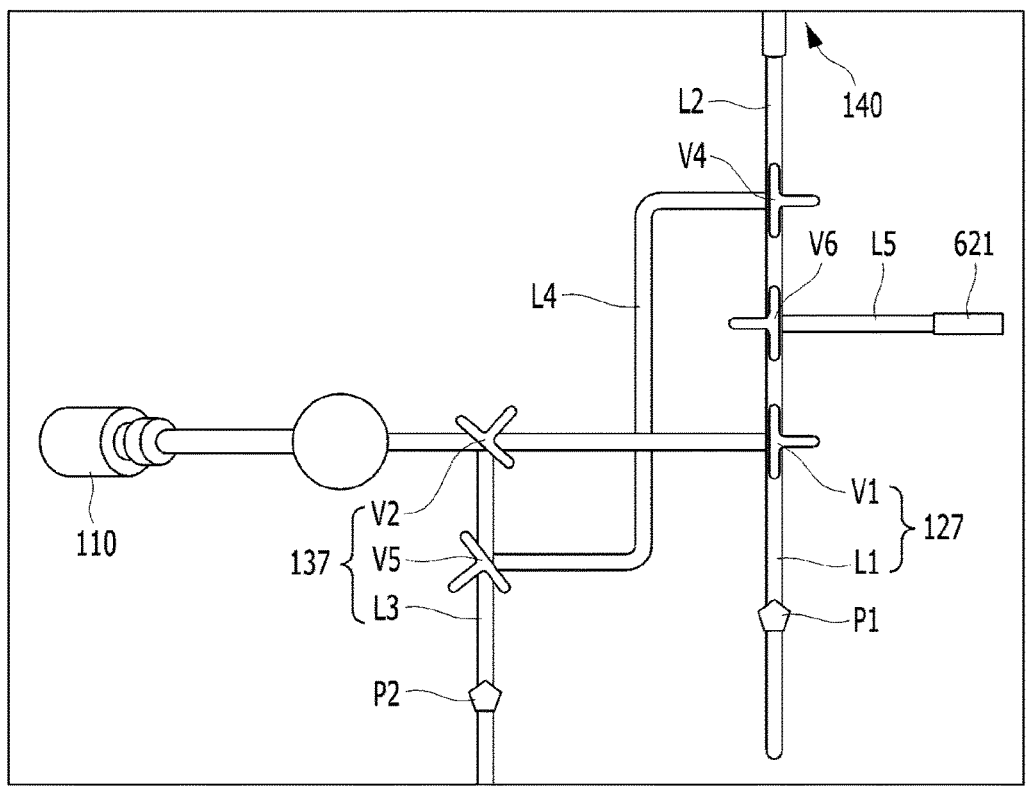

Also, as shown in FIG. 25, when the first valve V1 is opened to connect the first path L1 and the second path L2 and the sixth valve V6 and the fourth valve V4 also open the second path L2, the mixed solution of the object and the saline solution is supplied from the inner mixing container 122 to the injection unit 140.

Figure 26:
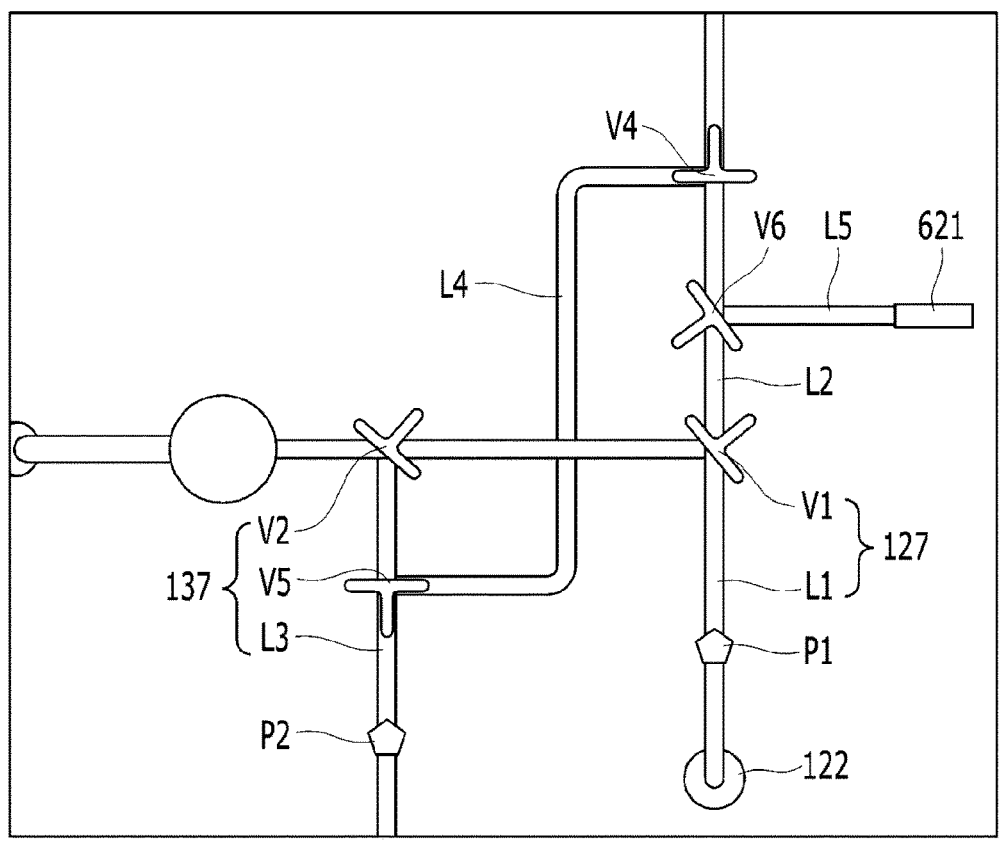

When the mixed solution is completely injected, as shown in FIG. 26, the fourth valve V4 is opened to connect the injection unit 140 and the storage container, and thus the saline solution is supplied along with a part of the remaining object on the second path L2 through the fourth path L4, and all injections are completed.

Figure 27:
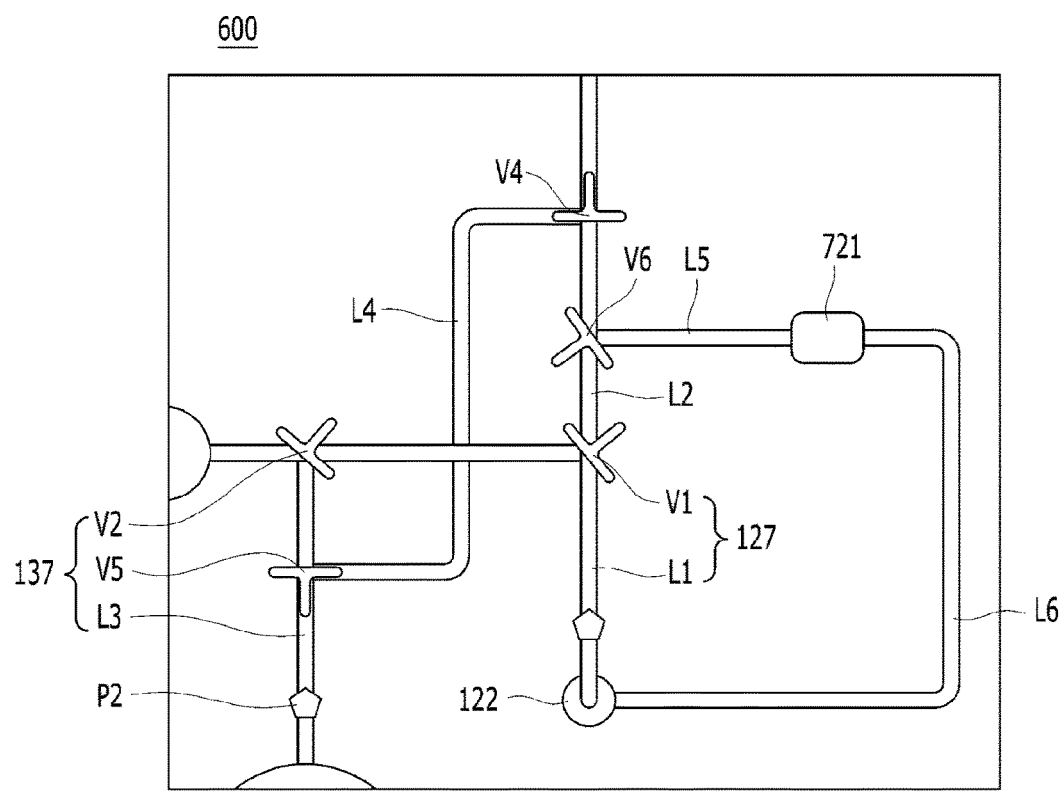
FIG. 27 is a schematic view of a radiopharmaceutical distribution device according to a sixth embodiment of the present invention.

FIG. 27 is a reference view illustrating a radiopharmaceutical distribution device 600 according to a sixth embodiment of the present invention. Hereinafter, the same reference numerals as the above-described reference numerals denote the same components.

Referring to FIG. 27, the radiopharmaceutical distribution device 600 according to the sixth embodiment of the present invention includes a sixth path L6 having one end connected to the fourth outer mixing container 621 and the other end connected to the inner mixing container 122.

In this case, while the mixed solution is controlled to be circulated from the inner mixing container 122 to the inner mixing container 122 again through the first valve V1, the sixth valve V6, and the sixth path L6 by suction force of the first pump P1, the object and the saline solution are mixed.

Since a method of discharging the remaining object is performed in the same manner as in the above-described fifth embodiment, redundant description will be omitted.

Therefore, the object and the saline solution are further easily mixed, and a mixing time can be reduced.

Figure 28:
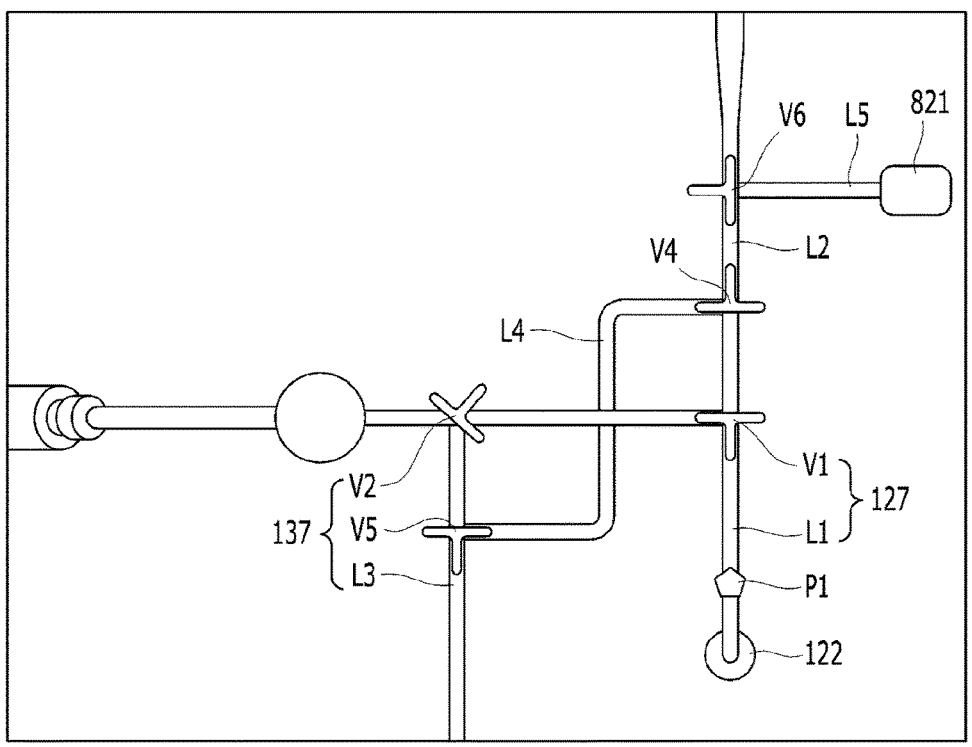
FIG. 28 is a schematic view of a radiopharmaceutical distribution device according to a seventh embodiment of the present invention.

FIG. 28 is a reference view illustrating a radiopharmaceutical distribution device 700 according to a seventh embodiment of the present invention. Hereinafter, the same reference numerals as the above-described reference numerals denote the same components.

Referring to FIG. 28, the radiopharmaceutical distribution device 700 according to the seventh embodiment of the present invention further includes a fourth valve V4 provided on the second path L2, a fifth valve V5 provided on the third path L3, and a fourth path L4 having one end connected with the fourth valve V4 and the other end connected with the fifth valve V5, and includes a sixth valve V6 arranged on the second path L2 and provided to be adjacent to the fourth valve V4 between the fourth valve V4 and the injection unit 140, a fifth path L5 having one end coupled to the sixth valve V6, and a fifth outer mixing container 721 coupled to be in communication with the other end of the fifth path L5 and flexibly increasing its volume so that the saline solution or the object supplied from the first pump P1 is temporarily stored when the sixth valve V6 opens the second path L2 and the fifth path L5 to be in communication with each other.

As a movement route of the object is described through the configuration, as shown in FIG. 28, after the object is temporarily stored in the inner mixing container 122, while the first valve V1 is opened to connect the inner mixing container 122 and the fourth valve V4, the object or the mixed solution of the object and the saline solution is mixed by repeatedly moving between the fifth outer mixing container 721 and the inner mixing container 122 by bidirectional suction force of the first pump P1.

Also, when the first valve V1 is opened to connect the first path L1 and the second path L2 and the sixth valve V6 and the fourth valve V4 also open the second path L2, the mixed solution in which the object and the saline solution are mixed is supplied from the inner mixing container 122 to the injection unit 140.

When the mixed solution is completely injected, the fourth valve V4 is opened to connect the injection unit 140 and the storage container, and thus the saline solution is supplied along with a part of the remaining object on the second path L2 through the fourth path L4, and all injection are completed.

When the object and the saline solution are mixed and supplied, since the mixed solution with a further uniform density is supplied, the object may be further stably supplied. Also, since radioactivity of the object left after the object is discharged from the inner mixing container 122 is measured, it is not necessary to measure radioactivity of an additionally discharged object, and thus it is expected to have an effect of precisely and stably supply and distribute the object.

While the present invention has been described with reference to the embodiments illustrated in the drawings, these are only examples. It may be understood by those skilled in the art that various modifications and equivalent other embodiments may be made. Therefore, the scope of the present invention is defined by the appended claims.

The invention claimed is:

1. A radiopharmaceutical distribution device, comprising:
a vial configured to store an object selected from a radiopharmaceutical or a radioactive isotope;
an object supply unit configured to check radioactivity by extracting a set amount of the object stored in the vial, and temporarily store or discharge the object extracted from the vial;
a saline solution supply unit selectively in communication with the object supply unit and configured to discharge a saline solution to be mixed with the object extracted from vial; and
an injection unit configured to store the object discharged from the object supply unit and the saline solution with a set volume discharged from the saline solution supply unit, in a mixed state,
wherein the object supply unit includes:
a measuring unit configured to check radioactivity by receiving the object extracted from the vial;
an inner mixing container arranged in the measuring unit to temporarily store the received object and configured to allow a volume of the stored object or the saline solution to be variable;
a first pump configured to suck the object from the inner mixing container and discharge the object; and
a first control unit configured to control a movement route of the object discharged or introduced through the first pump,
wherein the inner mixing container is made of an elastic material to allow a volume of the object or the saline solution to be flexibly changed when the object or the saline solution is temporarily stored,
wherein the saline solution supply unit is provided to remove air in the injection unit and to supply the saline solution to the injection unit, and the saline solution supply unit comprises:

a storage container configured to store the saline solution;

a second pump configured to suck the saline solution from the storage container and discharge the saline solution; and a second control unit configured to control a movement route of the saline solution discharged through the second pump, wherein the first control unit includes:
a first path connecting the vial with the inner mixing container;
a second path having one end connected with the first path between the vial and the inner mixing container and the other end on which the injection unit is arranged; and
a first valve arranged at a portion at which the first path and the second path are connected to set an opening and closing direction of the first path and the second path, wherein the second control unit comprises:
a third path having one end connected to the first path between the vial and the first valve; and
a second valve arranged at a portion at which the first path and the third path are connected to set an opening and closing direction of the first path and the third path, and wherein the first control unit further includes
a first outer mixing container provided to be in communication with the first path between the first valve and the first pump, and configured to flexibly increase its volume so that the saline solution or the object supplied from the first pump is temporarily stored when the first valve is closed in every direction.

2. The radiopharmaceutical distribution device of claim 1, further comprising an expansion preventing unit arranged at an outside of the first outer mixing container and configured to prevent a volume of the first outer mixing container from being flexibly increased when the first valve is opened in one direction.

3. The radiopharmaceutical distribution device of claim 1, wherein the first control unit further includes:
a third valve arranged between the vial and the second valve to set an opening and closing direction of the first path; and
a second outer mixing container provided to be in communication with the first path between the second valve and the third valve, and configured to flexibly increase its volume so that the saline solution or the object supplied from the first pump is temporarily stored when the third valve is closed.

4. The radiopharmaceutical distribution device of claim 3, further comprising:
a fourth valve provided on the second path;
a fifth valve provided on the third path;
a fourth path having one end connected with the fourth valve and the other end connected with the fifth valve; and
a third outer mixing container provided to be in communication with the second path between the first valve and the fourth valve, and configured to flexibly increase its volume so that a mixed solution or the object supplied from the first pump is temporarily stored when the fourth valve is closed in every direction.

5. The radiopharmaceutical distribution device of claim 3, further comprising:
a fourth valve provided on the second path;
a fifth valve provided on the third path;
a fourth path having one end connected with the fourth valve and the other end connected with the fifth valve;
a sixth valve arranged on the second path and provided to be adjacent to the fourth valve between the first valve and the fourth valve;
a fifth path having one end coupled to the sixth valve; and
a fourth outer mixing container coupled to be in communication with the other end of the fifth path, and configured to flexibly increase its volume so that the saline solution or the object supplied from the first pump is temporarily stored when the sixth valve is opened so that the second path and the fifth path are in communication with each other.

6. The radiopharmaceutical distribution device of claim 5, further comprising:
a sixth path having one end connected to the fourth outer mixing container and the other end connected to the inner mixing container,
wherein the object or the saline solution is controlled to be circulated from the inner mixing container to the inner mixing container again through the first valve, the sixth valve, and the sixth path by suction force of the first pump.

7. The radiopharmaceutical distribution device of claim 3, further comprising:
a fourth valve provided on the second path;
a fifth valve provided on the third path;
a fourth path having one end connected with the fourth valve and the other end connected with the fifth valve;
a sixth valve arranged on the second path and provided to be adjacent to the fourth valve between the fourth valve and the injection unit;
a fifth path having one end connected to the sixth valve; and
a fifth outer mixing container coupled to be in communication with the other end of the fifth path and configured to flexibly increase its volume so that the saline solution or the object supplied from the first pump is temporarily stored when the sixth valve opens the second path and the fifth path.

8. The radiopharmaceutical distribution device of claim 1, further comprising
an injector configured to store the object or a mixed solution of the object and the saline solution and
a cover member coupled to be attached to or detached from the injector and covering an outside of the injector to shield radioactivity emitted from the object stored in the injector,
wherein the injector includes:
a main body including an inlet, provided on one end thereof to store the object or the mixed solution in the main body, and made of a transparent or translucent material;
a push rod partially or entirely inserted into the main body, and configured to pressurize pressurizing the mixed solution or the object stored in the main body to be discharged to the outside of the injector through the inlet by reciprocating;
a first support member coupled to the other end of the main body and protruding to be fixed to an inside of the cover member;
a second support member coupled at one end of the push rod to be opposite to the first support member and protruding to be fixed to the inside of the cover member; and a cap selectively coupled to the inlet and preventing the saline solution or the object stored in the main body from being leaked to the outside of the injector.

9. The radiopharmaceutical distribution device of claim 8, wherein the cover member includes
   a first shield member provided to cover one side of the injector and having an exposure hole so that the other end of the main body or a part of the cap is exposed to the outside of the injector; and
   a second shield member slidably coupled on the first shield member and provided to selectively cover the other side of the injector.

10. The radiopharmaceutical distribution device of claim 9, further comprising
    a capturing unit arranged to be adjacent to the other end of the main body, and configured to capture a state in which the object or the saline solution is supplied to the injector.

11. The radiopharmaceutical distribution device of claim 10, wherein the capturing unit comprises
    a lens member configured to capture an image of the saline solution or the object injected into the other end of the main body,
    a plurality of mirror members provided so that the lens member can capture an indirectly reflected phase, and
    a sensor member configured to detect whether the saline solution or the object injected into the other end of the main body approaches a set range by reading the image captured through the lens member.

* * * * *